United States Patent
Yu et al.

(10) Patent No.: US 10,617,459 B2
(45) Date of Patent: Apr. 14, 2020

(54) ENDOVASCULAR NEAR CRITICAL FLUID BASED CRYOABLATION CATHETER HAVING PLURALITY OF PREFORMED TREATMENT SHAPES

(71) Applicant: ADAGIO MEDICAL, INC., Laguna Hills, CA (US)

(72) Inventors: Xiaoyu Yu, Laguna Hills, CA (US); Steven Kovalcheck, Laguna Hills, CA (US); Alexei Babkin, Laguna Hills, CA (US)

(73) Assignee: Adagio Medical, Inc., Laguna Hills, CA (US)

( * ) Notice: Subject to any disclaimer, the term of this patent is extended or adjusted under 35 U.S.C. 154(b) by 476 days.

(21) Appl. No.: 15/304,524

(22) PCT Filed: Apr. 7, 2015

(86) PCT No.: PCT/US2015/024778
§ 371 (c)(1),
(2) Date: Oct. 15, 2016

(87) PCT Pub. No.: WO2015/160574
PCT Pub. Date: Oct. 22, 2015

(65) Prior Publication Data
US 2017/0049495 A1   Feb. 23, 2017

Related U.S. Application Data

(60) Provisional application No. 61/981,110, filed on Apr. 17, 2014.

(51) Int. Cl.
*A61B 18/02* (2006.01)
*A61B 18/00* (2006.01)

(52) U.S. Cl.
CPC .... *A61B 18/02* (2013.01); *A61B 2018/00351* (2013.01); *A61B 2018/00357* (2013.01);
(Continued)

(58) Field of Classification Search
CPC .... A61B 2018/0293; A61B 2018/0212; A61B 18/02
See application file for complete search history.

(56) References Cited

U.S. PATENT DOCUMENTS 3,062,017 A   11/1962   Balcar
3,613,689 A   10/1971   Crump
(Continued)

FOREIGN PATENT DOCUMENTS

GB   1422535   1/1976
GB   2283678   6/1996
(Continued)

OTHER PUBLICATIONS

Stuehlinger, M., et al., "CoolLoop First: A First in Man Study to Test a Novel Circular Cryoablation System in Paroxysmal Artial Fibrillation," Journal of Artial Fibrillation, vol. 81, Issue 3, Oct.-Nov. 2015.
(Continued)

*Primary Examiner* — Linda C Dvorak
*Assistant Examiner* — Annabeth E Rodriguez
(74) *Attorney, Agent, or Firm* — Richard Batt

(57) ABSTRACT

An endovascular near critical fluid based cryoablation catheter for creating an elongate lengthwise-continuous lesion in tissue comprises an elongate shaft, a flexible distal tissue treatment section, and a distal tip. A plurality of flexible tubes extend through the distal treatment section to transport a near critical fluid to and from the distal tip. The distal treatment section is controllably deployed to match the contour of an anatomical region to be treated. In embodi-
(Continued)

ments the distal treatment section includes a superelastic material and can assume a plurality of different shapes based on the distance ejected from an outer sleeve member. When the catheter is activated, heat is transferred between a target tissue and the distal treatment section of the catheter thereby creating the elongate lengthwise-continuous lesion in the tissue.

14 Claims, 19 Drawing Sheets

(52) U.S. Cl.
CPC .............. *A61B 2018/00363* (2013.01); *A61B 2018/00577* (2013.01); *A61B 2018/0212* (2013.01); *A61B 2018/0262* (2013.01)

(56) References Cited

U.S. PATENT DOCUMENTS

| | | | |
|---|---|---|---|
| 3,889,680 A | 6/1975 | Armao | |
| 3,942,010 A | 3/1976 | Peterson | |
| 3,993,123 A | 11/1976 | Chu | |
| 4,034,251 A | 7/1977 | Haas | |
| 4,167,771 A | 9/1979 | Simons | |
| 4,226,281 A | 10/1980 | Chu | |
| 4,281,268 A | 7/1981 | Sawa | |
| 4,384,360 A | 5/1983 | Kitadate | |
| 4,418,421 A | 11/1983 | Kitadate | |
| 4,519,389 A | 5/1985 | Gudkin | |
| 4,548,045 A | 10/1985 | Altares | |
| 4,802,475 A | 2/1989 | Weshahy | |
| 4,838,041 A | 6/1989 | Bellows | |
| 4,843,446 A | 6/1989 | Nishino | |
| 4,945,562 A | 7/1990 | Staub | |
| 4,946,460 A | 8/1990 | Merry | |
| 4,982,080 A | 1/1991 | Wilson | |
| 5,012,505 A | 4/1991 | Zupancic | |
| 5,037,395 A | 8/1991 | Spencer | |
| 5,108,390 A | 4/1992 | Potocky | |
| 5,147,355 A | 9/1992 | Friedman | |
| 5,147,538 A | 9/1992 | Wright | |
| 5,155,093 A | 10/1992 | Den | |
| 5,173,606 A | 12/1992 | Weinberger | |
| 5,211,646 A | 5/1993 | Alperovich | |
| 5,212,626 A | 5/1993 | Bell | |
| 5,214,925 A | 6/1993 | Hoy | |
| 5,237,824 A | 8/1993 | Pawliszyn | |
| 5,254,116 A | 10/1993 | Baust | |
| 5,274,237 A | 12/1993 | Gallagher | |
| RE34,502 E | 1/1994 | Webster | |
| 5,275,595 A | 1/1994 | Dobak, III | |
| 5,324,286 A | 6/1994 | Fowle | |
| 5,327,905 A * | 7/1994 | Avitall | A61B 18/1492 |
| | | | 600/381 |
| 5,334,181 A | 8/1994 | Rubinsky | |
| 5,369,384 A | 11/1994 | Woods | |
| 5,400,602 A | 3/1995 | Chang | |
| 5,405,533 A | 4/1995 | Hazleback | |
| 5,417,072 A | 5/1995 | Silver | |
| 5,433,717 A | 7/1995 | Rubinsky | |
| 5,452,582 A | 9/1995 | Longsworth | |
| 5,471,844 A | 12/1995 | Levi | |
| 5,494,039 A | 2/1996 | Onki | |
| 5,504,924 A | 4/1996 | Ohashi | |
| 5,520,682 A | 5/1996 | Baust | |
| 5,531,742 A | 7/1996 | Barken | |
| 5,573,532 A | 11/1996 | Chang | |
| 5,603,221 A | 2/1997 | Maytal | |
| 5,661,980 A | 9/1997 | Gallivan | |
| 5,702,435 A | 12/1997 | Maytal | |
| 5,716,353 A | 2/1998 | Matsura | |
| 5,733,280 A | 3/1998 | Avitall | |
| 5,741,248 A | 4/1998 | Stern | |
| 5,757,885 A | 5/1998 | Yao | |
| 5,800,487 A | 9/1998 | Mikus | |
| 5,800,488 A | 9/1998 | Crockett | |
| 5,816,052 A | 10/1998 | Foote | |
| 5,885,276 A | 3/1999 | Ammar | |
| 5,899,897 A | 5/1999 | Rabin | |
| 5,899,898 A | 5/1999 | Arless | |
| 5,899,899 A | 5/1999 | Arless | |
| 5,901,783 A | 5/1999 | Dobak, III | |
| 5,910,104 A | 6/1999 | Dobak, III | |
| 5,916,212 A | 6/1999 | Baust | |
| 5,924,975 A | 7/1999 | Goldowsky | |
| 5,947,960 A | 9/1999 | Griswold | |
| 5,950,444 A | 9/1999 | Matsunaga | |
| 5,957,963 A | 9/1999 | Dobak | |
| 5,978,697 A | 11/1999 | Maytal | |
| 5,993,444 A | 11/1999 | Ammar | |
| 5,997,781 A | 12/1999 | Nishikawa | |
| 6,004,269 A | 12/1999 | Crowley | |
| 6,039,730 A | 3/2000 | Rabin | |
| 6,074,412 A | 6/2000 | Mikus | |
| 6,096,068 A | 8/2000 | Dobak | |
| 6,106,518 A | 8/2000 | Wittenberger | |
| 6,139,544 A | 10/2000 | Mikus | |
| 6,142,991 A | 11/2000 | Schatzberger | |
| 6,161,543 A * | 12/2000 | Cox | A61B 17/00234 |
| | | | 128/898 |
| 6,171,277 B1 | 1/2001 | Ponzi | |
| 6,179,831 B1 | 1/2001 | Bilweis | |
| 6,182,666 B1 | 2/2001 | Dobak, III | |
| 6,190,378 B1 | 2/2001 | Jarvinen | |
| 6,190,382 B1 | 2/2001 | Ormsby | |
| 6,193,644 B1 | 2/2001 | Dobak, III | |
| 6,198,974 B1 | 3/2001 | Webster | |
| 6,235,018 B1 | 5/2001 | Lepivert | |
| 6,237,355 B1 | 5/2001 | Li | |
| 6,241,722 B1 | 6/2001 | Dobak | |
| 6,251,105 B1 | 6/2001 | Mikus | |
| 6,263,046 B1 | 7/2001 | Rogers | |
| 6,270,493 B1 | 8/2001 | Lalonde | |
| 6,307,916 B1 | 10/2001 | Rogers | |
| 6,324,852 B1 | 12/2001 | Cheng | |
| 6,341,629 B1 | 1/2002 | Clark | |
| 6,347,675 B1 | 2/2002 | Kolle | |
| 6,355,029 B1 | 3/2002 | Joye | |
| 6,368,304 B1 | 4/2002 | Aliberto | |
| 6,377,659 B1 | 4/2002 | Snyder | |
| 6,396,901 B1 | 5/2002 | Heil | |
| 6,432,174 B1 | 8/2002 | Heung | |
| 6,440,126 B1 | 8/2002 | Abboud | |
| 6,451,011 B2 | 9/2002 | Tu | |
| 6,471,694 B1 | 10/2002 | Kudaravalli | |
| 6,475,212 B2 | 11/2002 | Dobak | |
| 6,477,231 B2 | 11/2002 | Snyder | |
| 6,486,078 B1 | 11/2002 | Rangarajan | |
| 6,520,933 B1 | 2/2003 | Evans | |
| 6,527,765 B2 | 3/2003 | Kelman | |
| 6,530,420 B1 | 3/2003 | Takada | |
| 6,537,271 B1 | 3/2003 | Murray | |
| 6,544,176 B2 | 4/2003 | Mikus | |
| 6,551,309 B1 | 4/2003 | LePivert | |
| 6,554,797 B1 | 4/2003 | Worthen | |
| 6,572,610 B2 | 6/2003 | Kovalcheck | |
| 6,584,332 B2 | 6/2003 | Yoshitake | |
| 6,602,276 B2 | 8/2003 | Dobak, III | |
| 6,622,494 B1 | 9/2003 | Pourrahimi | |
| 6,622,507 B2 | 9/2003 | Cotte | |
| 6,628,002 B2 | 9/2003 | Ritz | |
| 6,648,879 B2 | 11/2003 | Joye | |
| 6,685,720 B1 | 2/2004 | Wu | |
| 6,706,037 B2 | 3/2004 | Zvuloni | |
| 6,726,653 B2 | 4/2004 | Noda | |
| 6,737,225 B2 | 5/2004 | Miller | |
| 6,746,445 B2 | 6/2004 | Abboud | |
| 6,767,346 B2 | 7/2004 | Damasco | |
| 6,812,464 B1 | 11/2004 | Sobolewski | |
| 6,848,502 B2 | 1/2005 | Bishop | |
| 6,848,458 B1 | 2/2005 | Shrinivasan | |
| 6,893,419 B2 | 5/2005 | Noda | |

(56) References Cited

U.S. PATENT DOCUMENTS

| | | |
|---|---|---|
| 6,893,433 B2 | 5/2005 | Lentz |
| 6,905,492 B2 | 6/2005 | Zvuloni |
| 6,936,045 B2 | 8/2005 | Yu |
| 6,941,953 B2 | 9/2005 | Feld |
| 6,989,009 B2 | 1/2006 | Lafontaine |
| 7,004,937 B2 | 2/2006 | Lentz |
| 7,022,120 B2 | 4/2006 | Lafontaine |
| 7,083,612 B2 | 8/2006 | Littrup |
| 7,110,506 B2 | 9/2006 | Radley |
| 7,160,290 B2 | 1/2007 | Eberl |
| 7,220,252 B2 | 5/2007 | Shah |
| 7,220,257 B1 | 5/2007 | Lafontaine |
| 7,195,625 B2 | 7/2007 | Lentz |
| 7,258,161 B2 | 8/2007 | Cosley et al. |
| 7,273,479 B2 | 9/2007 | Littrup et al. |
| 7,410,484 B2 | 8/2008 | Littrup et al. |
| 7,648,497 B2 | 1/2010 | Lane et al. |
| 7,706,894 B2 * | 4/2010 | Stewart .............. A61B 18/1492 607/122 |
| 7,740,627 B2 | 6/2010 | Gammie et al. |
| 7,842,031 B2 | 11/2010 | Abboud et al. |
| 8,012,147 B2 | 9/2011 | Lafontaine |
| 8,177,780 B2 | 5/2012 | Cox |
| 8,298,217 B2 | 10/2012 | Lane |
| 8,387,402 B2 | 3/2013 | Littrup |
| 8,475,441 B2 | 7/2013 | Babkin |
| 8,641,704 B2 | 2/2014 | Werneth |
| 8,685,014 B2 | 4/2014 | Babkin |
| 8,740,891 B2 | 6/2014 | Babkin |
| 8,740,892 B2 | 6/2014 | Babkin |
| 8,845,628 B2 | 9/2014 | Babkin |
| 8,888,768 B2 | 11/2014 | Babkin |
| 8,945,106 B2 | 2/2015 | Arless |
| 9,095,320 B2 | 8/2015 | Littrup |
| 2001/0024485 A1 | 9/2001 | Rogers |
| 2001/0047134 A1 | 11/2001 | Holdaway |
| 2002/0049409 A1 | 4/2002 | Noda |
| 2002/0062831 A1 | 5/2002 | Beyar |
| 2002/0072741 A1 | 6/2002 | Silwa |
| 2002/0087151 A1* | 7/2002 | Mody ................ A61B 18/1492 606/15 |
| 2002/0087152 A1 | 7/2002 | Mikus |
| 2002/0151331 A1 | 10/2002 | Abdelmonem |
| 2003/0040740 A1 | 2/2003 | Kovalcheck |
| 2003/0055415 A1 | 3/2003 | Yu |
| 2003/0195605 A1 | 10/2003 | Kovalcheck |
| 2003/0199817 A1 | 10/2003 | Thompson |
| 2004/0027462 A1 | 2/2004 | Hing |
| 2004/0118144 A1 | 6/2004 | Hsu |
| 2004/0148004 A1 | 7/2004 | Wallsten |
| 2004/0215295 A1 | 10/2004 | Littrup |
| 2005/0027289 A1 | 2/2005 | Castellano |
| 2005/0209587 A1 | 9/2005 | Joye |
| 2005/0261573 A1 | 11/2005 | Littrup |
| 2006/0235375 A1 | 6/2006 | Littrup |
| 2006/0212028 A1 | 9/2006 | Joye |
| 2006/0235357 A1 | 10/2006 | Littrup |
| 2006/0247611 A1 | 11/2006 | Abboud |
| 2006/0253114 A1 | 11/2006 | Saadat |
| 2008/0119836 A1 | 5/2008 | Littrup |
| 2008/0312644 A1 | 12/2008 | Fourkas |
| 2009/0118723 A1 | 5/2009 | Lalonde |
| 2010/0057063 A1 | 3/2010 | Arless |
| 2010/0256621 A1 | 10/2010 | Babkin |
| 2011/0009854 A1 | 1/2011 | Babkin |
| 2011/0040297 A1* | 2/2011 | Babkin ................. A61B 18/02 606/21 |
| 2011/0054453 A1 | 3/2011 | Lalonde |
| 2011/0162390 A1 | 7/2011 | Littrup |
| 2011/0184399 A1 | 7/2011 | Wittenberger |
| 2012/0059364 A1 | 3/2012 | Baust |
| 2012/0109118 A1 | 5/2012 | Lalonde |
| 2012/0253336 A1 | 10/2012 | Littrup |
| 2013/0073014 A1 | 3/2013 | Lim |
| 2013/0197498 A1 | 8/2013 | Laske |
| 2013/0324987 A1 | 12/2013 | Leung |
| 2013/0331829 A1 | 12/2013 | Babkin |
| 2013/0345688 A1 | 12/2013 | Babkin |
| 2014/0364848 A1 | 12/2014 | Heimbecher |
| 2015/0250524 A1 | 9/2015 | Moriarty |

FOREIGN PATENT DOCUMENTS

| | | | |
|---|---|---|---|
| JP | 7-136180 | 5/1995 | |
| JP | 2008-515469 | 5/2008 | |
| WO | WO1993008751 | 5/1993 | |
| WO | WO1997049344 | 12/1997 | |
| WO | WO-0136016 A3 * | 3/2002 | ......... A61B 18/1492 |
| WO | WO2002058576 | 8/2002 | |
| WO | WO2002096270 | 12/2002 | |
| WO | WO2002011638 | 4/2003 | |
| WO | 2004/064914 | 8/2004 | |
| WO | WO2004064914 | 3/2005 | |
| WO | 2009/009398 | 1/2009 | |
| WO | WO2009067497 | 5/2009 | |
| WO | WO-2012058430 A2 * | 5/2012 | ............ A61B 18/02 |
| WO | WO2013013098 | 1/2013 | |
| WO | WO2013013099 | 1/2013 | |
| WO | WO2015160574 | 10/2015 | |

OTHER PUBLICATIONS

Skanes, Allan C., et al., "Cryoblation: Potentials and Pitfalls," doi:10.1046/j.1540-8167.2004.15106.x, Jul. 6, 2004.

Lemola, Kristina, MD, et al., "Pulmonary Vein Isolation as an End Point for Left Atrial Circumferential Ablation of Atrial Fibrillation," Journal of American College of Cardiology, vol. 46, No. 6, 2005.

Rolf, Sascha, MD, et al., "Electroanatomical Mapping of Atrial Fibrillation: Review of the Current Techniques and Advances," Journal of Artrial Fibrillation, vol. 7, Issue 4, Dec. 2014-Jan. 2015.

International Search Report dated Dec. 28, 2016 for PCT/US2016/033833.

International Search Report dated Jan. 31, 2017 for PCT/US2016/051954.

International Search Report dated Feb. 2, 2017 for PCT/US2016/063882.

International Search Report dated Jan. 15, 2016 for PCT/US2015/056780.

Office Action dated Jul. 26, 2018 for U.S. Appl. No. 14/915,631.

Office Action dated Jul. 13, 2018 for U.S. Appl. No. 15/028,925.

Supplemental European Search Report dated Apr. 23, 2018 for EP15858716.

Australian Examination Report No. 1, dated Jul. 31, 2018 for 2014327045.

International Search Report dated Mar. 18, 2015 for PCT/US14/56839.

International Search Report dated Jan. 21, 2015 for PCT/US2014/059684.

International Search Report dated Oct. 1, 2012 for PCT/US2012/047487.

International Search Report /Written Opinion dated Jan. 14, 2009 for PCT/US2008/084004.

International Preliminary Examination Report dated Oct. 18, 2016 for PCT/US2015/024778.

European Search Report for EP04702597 dated Sep. 18, 2007.

European Search Report for EP08852254 dated Nov. 19, 2010.

European Search Report for EP05858178.6 dated Nov. 5, 2010.

European Search Report for EP10184565 dated Feb. 21, 2011.

Arai, Y., et al., "Supercritical Fluids," pp. 161 and 199, ISBN 3540412484, Springer 2002.

Barron, Randall F., "Cryogenic Heat Transfer," pp. 97, 129 and 130, Taylor & Francis, 1999.

Lide, D.R. and Keihiaian, H.V., "CRC Handbook of Thermophysical and Thermochemical Data," p. 375, CRC Press 1994.

Sun, Ya-ping, Supercritical Fluid Technology in Materials Science and Engineering, pp. 1 and 26, CRC Press 2002.

(56) References Cited

OTHER PUBLICATIONS

Thakore, S.B. and Bhatt, B.I., "Introduction to Process Engineering and Design," Chemical Engineering Series, pp. 27-28, McGraw-Hill 2008.

\* cited by examiner

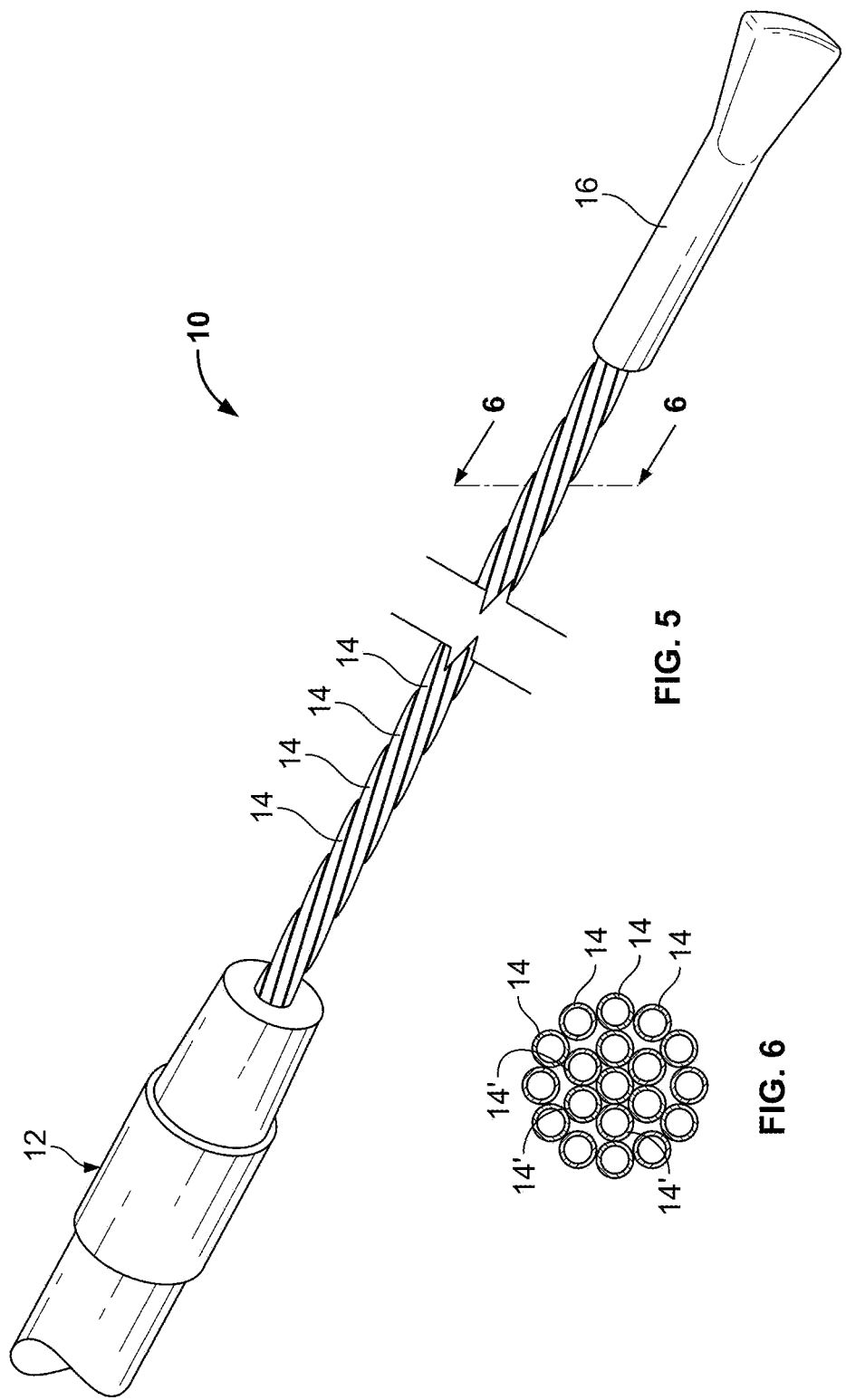

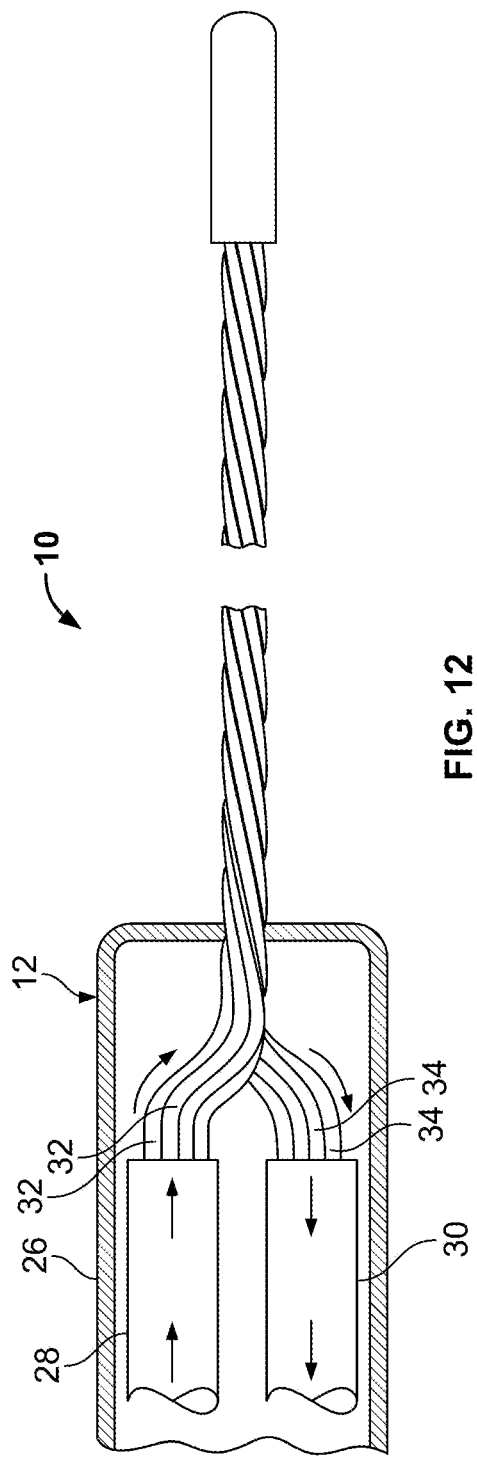
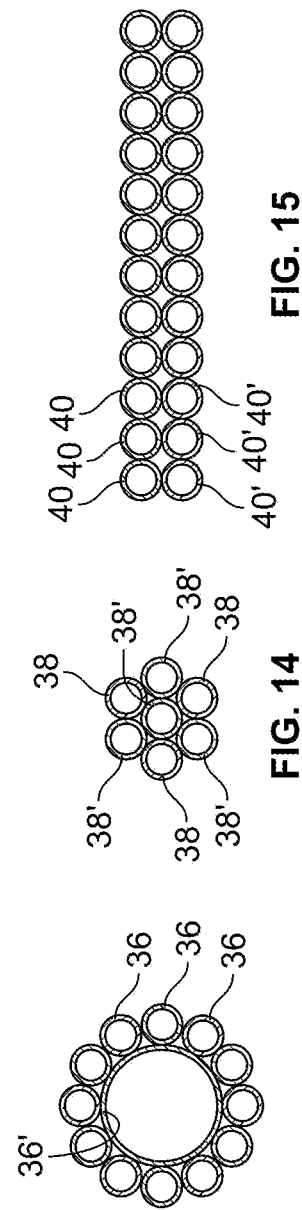
FIG. 12
FIG. 13
FIG. 14
FIG. 15

ENDOVASCULAR NEAR CRITICAL FLUID BASED CRYOABLATION CATHETER HAVING PLURALITY OF PREFORMED TREATMENT SHAPES

CROSS-REFERENCE TO RELATED APPLICATIONS

This application is a US 371 National Phase filing of International PCT Patent Application No. PCT/US2015/024778, filed on Apr. 7, 2015, which claims priority to U.S. provisional patent application 61/981,110, filed Apr. 17, 2014, entitled "ENDOVASCULAR NEAR CRITICAL FLUID BASED CRYOABLATION CATHETER HAVING PLURALITY OF PREFORMED TREATMENT SHAPES".

BACKGROUND OF THE INVENTION

1. Field of the Invention

This invention relates to cryosurgery and more particularly to cryoablation catheters comprising a fluid operating near its critical point.

2. Description of the Related Art

Cryosurgery is a promising approach for treating various medical conditions, none of which are less important than the treatment of an abnormal heart beat.

Atrial flutter and atrial fibrillation are heart conditions in which the left or right atrium of the heart beat improperly. Atrial flutter is a condition when the atria beat very quickly, but still evenly. Atrial fibrillation is a condition when the atria beat very quickly, but unevenly.

These conditions are often caused by aberrant electrical behavior of some portion of the atrial wall. Certain parts of the atria, or nearby structures such as the pulmonary veins, can misfire in their production or conduction of the electrical signals that control contraction of the heart, creating abnormal electrical signals that prompt the atria to contract between normal contractions caused by the normal cascade of electrical impulses. This can be caused by spots of ischemic tissue, referred to as ectopic foci, or by electrically active fibers in the pulmonary veins, for example.

Currently, the Cox Maze procedure, developed by Dr. James Cox in the 1980's, is a method for eliminating atrial fibrillation. In the Cox Maze procedure, the atrial wall is cut with a scalpel in particular patterns which isolate the foci of arrhythmia from the rest of the atrial wall, and then sewn back together. Upon healing, the resultant scar tissue serves to interrupt ectopic re-entry pathways and other aberrant electrical conduction and prevent arrhythmia and fibrillation. There are several variations of the Cox maze procedure, each involving variations in the number and placement of lesions created.

The original Cox maze procedure was an open chest procedure requiring surgically opening the atrium after opening the chest. The procedure itself has a high success rate, though due to the open chest/open heart nature of the procedure, and the requirement to stop the heart and establish a coronary bypass, it is reserved for severe cases of atrial fibrillation.

The Cox maze procedure has been performed using ablation catheters in both transthoracic epicardial approaches and transvascular endocardial approaches. In transthoracic epicardial approaches, catheters or small probes are used to create linear lesions in the heart wall along lines corresponding to the maze of the Cox maze procedure. In the transvascular endocardial approaches, a catheter is navigated through the vasculature of the patient to the atrium, pressed against the inner wall of the atrium, and energized to create lesions corresponding to the maze of the Cox maze procedure.

In either approach, various ablation catheters have been proposed for creation of the lesion, including flexible cryoprobes or cryocatheters, bipolar RF catheters, monopolar RF catheters (using ground patches on the patient's skin), microwave catheters, laser catheters, and ultrasound catheters. U.S. Pat. No. 6,190,382 to Ormsby and U.S. Pat. No. 6,941,953 to Feld, for example, describe RF ablation catheters for ablating heart tissue. These approaches are attractive because they are minimally invasive and can be performed on a beating heart. However, these approaches have a low success rate. The low success rate may be due to incomplete lesion formation. A fully transmural lesion is required to ensure that the electrical impulse causing atrial fibrillation are completely isolated from the remainder of the atrium, and this is difficult to achieve with beating heart procedures.

A major challenge to the effective epicardial application of ablative energy sources to cardiac tissue without the use of the heart-lung machine ("off-pump") is that during normal heart function the atria are filled with blood at 37° C. that is moving through the atria at roughly 5 liters per minute. If cryothermia energy is applied epicardially, this atrial blood flow acts as a "cooling sink," warming the heart wall and making it difficult to lower the endocardial surface of the atrial wall to a lethal temperature (roughly −30° C.). Thus, lesion transmurality is extremely difficult to attain.

Similarly, if heat-based energy sources such as RF, microwave, laser, or HIFU are applied to the epicardial surface without using the heart-lung machine to empty the atria, the blood flowing through the atrium acts as a heat sink, cooling the heart wall making it difficult to raise the endocardial surface of the atrial wall to a lethal temperature (roughly 55° C.).

Another shortcoming with certain cryosurgical apparatus arises from evaporation. The process of evaporation of a liquefied gas results in enormous expansion as the liquid converts to a gas; the volume expansion is on the order of a factor of 200. In a small-diameter system, this degree of expansion consistently results in a phenomenon known in the art as "vapor lock." The phenomenon is exemplified by the flow of a cryogen in a thin-diameter tube, such as is commonly provided in a cryoprobe. A relatively massive volume of expanding gas that forms ahead of it impedes the flow of the liquid cryogen.

Traditional techniques that have been used to avoid vapor lock have included restrictions on the diameter of the tube, requiring that it be sufficiently large to accommodate the evaporative effects that lead to vapor lock. Other complex cryoprobe and tubing configurations have been used to "vent" $N_2$ gas as it formed along transport tubing. These designs also contributed to limiting the cost efficacy and probe diameter.

Due to the nature of the procedure and anatomical locations that lesions must be placed, the cryoprobe must be sufficiently flexible by the surgeon to be placed on the correct location of the heart surface.

Malleable and flexible cryoprobes are described in U.S. Pat. Nos. 6,161,543 and 8,177,780, both to Cox et al. The described probe has a malleable shaft. In embodiments, a malleable metal rod is coextruded with a polymer to form the shaft. The malleable rod permits the user to plastically deform the shaft into a desired shape so that a tip can reach the tissue to be ablated.

U.S. Pat. No. 5,108,390, issued to Potocky et al, discloses a highly flexible cryoprobe that can be passed through a blood vessel and into the heart without external guidance other than the blood vessel itself.

Several patents disclose the use of bellows-type assemblies for use with cryoablation systems. For example, U.S. Pat. No. 6,241,722, issued to Dobak et al, discloses a cryogenic catheter with a bellows and which utilizes a longitudinally movable Joule-Thomson nozzle of expansion. The Dobak '722 device preferably uses closed media-flow pathways for recycling of the media employed.

Dobak et al, in U.S. Pat. No. 5,957,963, disclose the use of a flexible catheter inserted through the vascular system of a patient to place the distal tip of the catheter in an artery feeding a selected organ of the patient. The '963 patent discloses a heat transfer bellows for cooling the blood flowing through the artery.

U.S. Pat. No. 6,767,346, issued to Damasco et al, entitled, "Cryosurgical Probe With Bellows Shaft", discloses use of a cryosurgical probe with a bellows shaft. U.S. Pat. No. 6,936,045, issued to Yu et al, entitled, "Malleable Cryosurgical Probe" discloses a cryosurgical probe used for Joule-Thomson nozzles.

CryoCath Technologies, Inc., Montreal, Quebec, Canada, utilizes a cryoablation probe trademarked under the name Surgifrost® which involves the use of a cryoprobe with a malleable or corrugated shell.

A problem with this and other similar products, however, is that these cryoprobes are not sufficiently flexible during use. Cryogenic temperatures tend to make metals and alloys more rigid, and less flexible. Such cryoprobes and catheters may not be articulated nor have the flexibility to form the necessary and desired shape when a cryogenic fluid is circulated through the treatment section of the apparatus. As a result, there is often an incomplete/intermittent thermal contact along the whole line of freezing. The small contact area provides a limitation for the power delivered to the tissue.

Additionally, there are substantial limits on flexibility and conformability of the treatment regions of the cryoablation apparatus. If the distal treatment section is too delicate and a breach in the cover occurs, cryogen may leak into the bloodstream. Substantial danger may result, perhaps death. Bubbles and/or cryogen in the heart, for example, may be immediately sent to the vessels in the brain. Such circumstances may result in highly undesirable neuro-ischemic events.

Various others have attempted to reduce the likelihood of a cryogenic fluid leaking into the bloodstream. U.S. Pat. No. 7,648,497 to Lane, for example, provides a second balloon surrounding a first balloon. The space between the first balloon and the second balloon is under vacuum. However, use of vacuum is undesirable because it is a very weak thermal conductor. Use of a weak thermal conductor reduces cooling power.

There is accordingly a need for improved methods and systems for providing minimally invasive, safe and efficient cryogenic cooling of tissues.

SUMMARY OF THE INVENTION

An endovascular near critical fluid based cryoablation catheter for creating elongate lengthwise-continuous lesions in tissue has an elongated shaft and a distal treatment section. At least one fluid delivery tube extends through the distal treatment section to transport a near critical fluid towards the distal tip. The catheter further includes at least one fluid return tube extending through the distal treatment section to transport the near critical fluid away from the distal tip. When activated, a flow of near critical fluid is circulated through the at least one fluid delivery tube and the at least one fluid return tube to transfer heat from the target tissue to the distal treatment section of the catheter thereby creating the elongated lengthwise-continuous lesion in the tissue.

The distal tissue treatment section may be controllably deployed or articulated. In one embodiment, the distal treatment section has a constrained state, and a plurality of unconstrained states different than the constrained state. Each of the unconstrained states has a curvature to match a particular anatomical curvature of a target tissue to be ablated.

In embodiments the distal treatment section has a bias, and springs back to its natural shape when unconstrained. An elongate constraining member such as an outer sheath is axially slideable relative to the distal treatment section to release the distal treatment section from the constrained state to one of the predetermined treatment shapes.

In embodiments a plurality of different shapes are formed by the distal treatment section. The various shapes are assumed or formed by the distal treatment section as the outer sheath is retracted. The plurality of shapes may take shape in sequence and are based on the travel distance that the inner shaft is ejected from the outer sheath.

The shapes may vary widely and include concave regions, convex regions, flat regions, looped sections, hooks, or circular portions. Additionally, the different shapes may reside in the same plane or different planes.

In embodiments the distal treatment section comprises a shape memory or superelastic material. A non-limiting exemplary superelastic material is Nitinol. In embodiments the at least one fluid delivery tube and the at least one fluid return tube comprises the superelastic material.

The length of the distal treatment section may vary. In embodiments the distal treatment section comprises a length ranging from 2 to 10 cm.

In embodiments the distal treatment section has a preset shape to match a specific lesion to be created. The distal treatment section has a treatment shape adapted to create a lesion spanning the atrium from above the right superior pulmonary vein entry to above the left superior pulmonary vein PV entry. Hereinafter the term "pulmonary vein" also being referred to as "PV".

In embodiments distal treatment section includes a tube bundle formed of a plurality of fluid return tubes and one or more fluid delivery tubes.

In embodiments the transport tubes are fluidly connected by an end cap. In other embodiments the transport tubes are fluidly connected by a U-turn.

In embodiments an endovascular near critical fluid based cryoablation method for creating an elongate lengthwise-continuous lesion in cardiac tissue comprises percutaneously inserting a catheter comprising a distal treatment section into a patient's vasculature. The method further comprises the step of navigating the distal treatment section to the heart, and through an opening in the heart until the distal treatment section is within a space in the heart.

The method further comprises deploying the distal treatment section of the catheter to make continuous contact along a curved target section of myocardial tissue.

In embodiments the distal treatment section is deployed by ejecting the distal treatment section a first travel length from the outer sheath such that the distal treatment section ejected from the outer sheath forms a first treatment shape.

The method further comprises contacting the first treatment shape with a first target section of cardiac tissue along an interior wall of the heart; and then creating a first elongate lengthwise-continuous lesion by circulating a near critical fluid through at least one fluid delivery tube and at least one fluid return tube extending through the distal treatment section.

In embodiments the distal treatment section is ejected a second travel length from the outer sheath such that the distal treatment section ejected from the outer sheath forms a second treatment shape, making continuous contact along a second target section of cardiac tissue along an interior wall of the heart; and creating a second elongate lengthwise-continuous lesion by circulating a near critical fluid through at least one fluid delivery tube and at least one fluid return tube extending through the distal treatment section.

The steps of ejecting are performed by retracting the outer sleeve over the elongate shaft to expose the distal treatment section.

In embodiments, at least one of the fluid delivery tube and the fluid return tube comprises a superelastic material.

In embodiments the distal treatment section further comprises a tubular member surrounding at least a portion of the fluid delivery tube and the fluid return tube. The tubular member can be, for example, a coil or spring.

In embodiments the activation of the cooling is halted when a threshold condition is met. The threshold condition is preferably one condition selected from the group consisting of: length of lesion, thickness of lesion, time elapsed, energy transferred, temperature change, pressure change, flowrate change, and power change.

In embodiments the step of creating the lesion may be performed by creating the lesion having a length ranging from 2 to 10 cm. The lesion may be formed to have a thickness extending the entire thickness of a heart wall for the entire length of the distal treatment section of the catheter in contact with the heart wall.

In embodiments the at least one of the first target section and the second target section is an interior linear section commencing near the IVC opening, and extending to the CTI.

In embodiments at least one of the first target section and the second target section is an interior linear section commencing above the right superior PV entry and extending to above the left superior PV entry.

In embodiments the at least one of the first and second target sections of cardiac tissue to be treated is curved.

In embodiments the at least one of the first and second target sections of cardiac tissue to be treated is concave, and at least one of the first and second target sections of cardiac tissue to be treated is convex.

In embodiments the method further comprises ejecting the distal treatment section a third travel length from the outer sheath such that the distal treatment section ejected from the outer sheath forms a third treatment shape, making continuous contact along a third target section of cardiac tissue along an interior wall of the heart; and creating a third elongate lengthwise-continuous lesion by circulating a near critical fluid through at least one fluid delivery tube and at least one fluid return tube extending through the distal treatment section.

In embodiments the second travel distance can be greater than the first travel distance, and the third travel distance can be greater than the second travel distance.

In embodiments at least one of the first, second, and third treatment shapes is flat.

In embodiments the first, second, and third treatment shapes are not in a single plane.

In embodiments the method further comprises partially ejecting the distal treatment section from an outer sleeve, and observing a location of distal treatment section under an imaging modality prior to activation.

BRIEF DESCRIPTION OF THE DRAWINGS

The description, objects and advantages of the present invention will become apparent from the detailed description to follow, together with the accompanying drawings wherein:

FIG. 5 is a perspective view of a cryoprobe;

FIG. 6 is a view taken along line 6-6 of FIG. 5;

FIG. 12 is a side view of another cryoprobe including a handle having an inlet shaft and outlet shaft therein;

FIGS. 13-15 are schematic cross sectional views showing example alternative arrangements of fluid transfer tubes.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Embodiments of the invention make use of thermodynamic processes using cryogens that provide cooling without encountering the phenomenon of vapor lock.

Cryogen Phase Diagram and Near Critical Point

Figure 1:
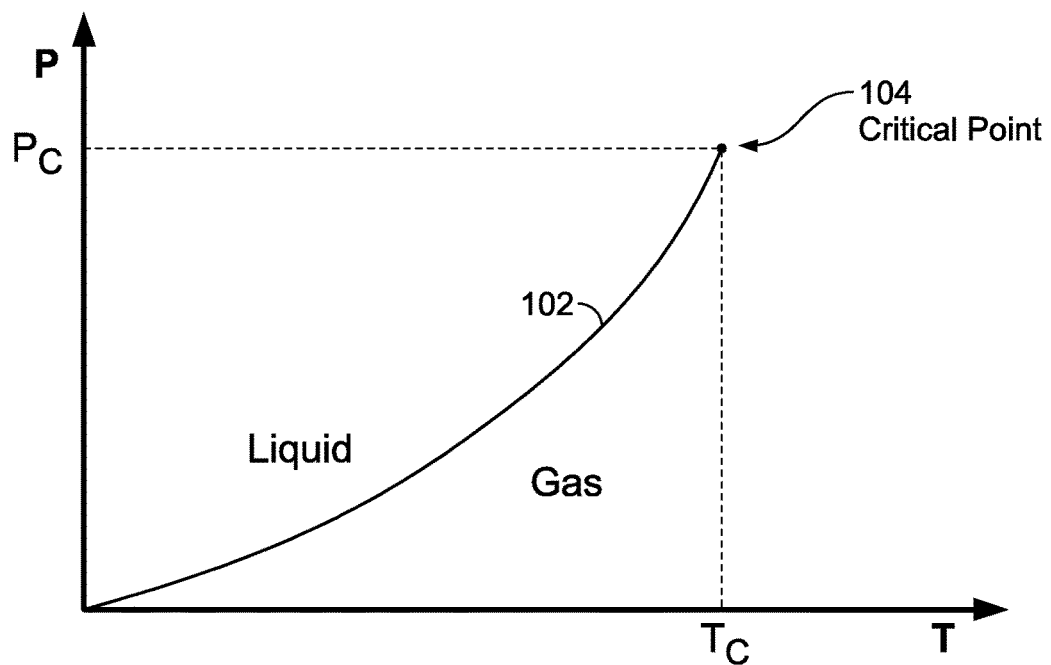
FIG. 1 illustrates a typical cryogen phase diagram.

This application uses phase diagrams to illustrate and compare various thermodynamic processes. An example phase diagram is shown in FIG. 1. The axes of the diagram correspond to pressure P and temperature T, and includes a phase line 102 that delineates the locus of all (P, T) points where liquid and gas coexist. For (P, T) values to the left of the phase line 102, the cryogen is in a liquid state, generally achieved with higher pressures and lower temperatures, while (P, T) values to the right of the phase line 102 define regions where the cryogen is in a gaseous state, generally achieved with lower pressures and higher temperatures. The phase line 102 ends abruptly in a single point known as the critical point 104. In the case of nitrogen $N_2$, the critical point is at $P_c$=33.94 bar and $T_c$=−147.15° C.

When a fluid has both liquid and gas phases present during a gradual increase in pressure, the system moves up along the liquid-gas phase line 102. In the case of $N_2$, the liquid at low pressures is up to two hundred times more dense than the gas phase. A continual increase in pressure causes the density of the liquid to decrease and the density of the gas phase to increase, until they are exactly equal only at the critical point 104. The distinction between liquid and gas disappears at the critical point 104. The blockage of forward flow by gas expanding ahead of the liquid cryogen is thus avoided by conditions surrounding the critical point, defined herein as "near-critical conditions." Factors that allow greater departure from the critical point while maintaining a functional flow include greater speed of cryogen flow, larger diameter of the flow lumen and lower heat load upon the thermal exchanger, or cryoprobe tip.

As the critical point is approached from below, the vapor phase density increases and the liquid phase density decreases until right at the critical point, where the densities of these two phases are exactly equal. Above the critical point, the distinction of liquid and vapor phases vanishes, leaving only a single, supercritical phase. All gases obey quite well the following van der Waals equation of state:

$$(p+3/v^2)(3v-1)=8t \quad [\text{Eq. 1}]$$

where $p=P/P_c$, $v=V/V_c$, and $t=T/T_c$, and $P_c$, $V_c$, and $T_c$ are the critical pressure, critical molar volume, and the critical temperature respectively.

The variables v, p, and t are often referred to as the "reduced molar volume," the "reduced pressure," and the "reduced temperature," respectively. Hence, any two substances with the same values of p, v, and t are in the same thermodynamic state of fluid near its critical point. Eq. 1 is thus referred to as embodying the "Law of Corresponding States." This is described more fully in H. E. Stanley, *Introduction to Phase Transitions and Critical Phenomena* (Oxford Science Publications, 1971), the entire disclosure of which is incorporated herein by reference for all purposes. Rearranging Eq. 1 provides the following expression for v as a function of p and t:

$$pv^3-(p+8t)v^2+9v-3=0. \quad [\text{Eq. 2}]$$

The reduced molar volume of the fluid v may thus be thought of as being an exact function of only the reduced pressure t and the reduced pressure p.

Typically, in embodiments of the invention, the reduced pressure p is fixed at a constant value of approximately one, and hence at a fixed physical pressure near the critical pressure, while the reduced temperature t varies with the heat load applied to the needle. If the reduced pressure p is a constant set by the engineering of the system, then the reduced molar volume v is an exact function of the reduced temperature t. In embodiments of the invention, the needle's operating pressure p may be adjusted so that over the course of variations in the temperature t of the needle, v is maintained below some maximum value at which the vapor lock condition will result. It is generally desirable to maintain p at the lowest value at which this is true since boosting the pressure to achieve higher values of p may involve use of a more complex and more expensive compressor, resulting in more expensive procurement and maintenance of the entire needle support system and lower overall wall plug efficiency. As used herein, "wall plug efficiency" refers to the total cooling power of the apparatus divided by the power obtained from a line to operate the system.

The conditions that need to be placed on v depend in a complex and non-analytic way on the volume flow rate dV/dt, the heat capacity of the liquid and vapor phases, and the transport properties such as the thermal conductivity, viscosity, etc., in both the liquid and the vapor. This exact relationship cannot be derived in closed form algebraically, but may be determined numerically by integrating the model equations that describe mass and heat transport within the needle. Conceptually, vapor lock occurs when the rate of heating of the needle produces the vapor phase, and when the cooling power of this vapor phase, which is proportional to the flow rate of the vapor times its heat capacity divided by its molar volume, is not able to keep up with the rate of heating to the needle. When this occurs, more and more of the vapor phase is formed in order to absorb the excess heat through the conversion of the liquid phase to vapor in the cryogen flow. This creates a runaway condition where the liquid converts into vapor phase to fill the needle, and effectively all cryogen flow stops due to the large pressure that results in this vapor phase as the heat flow into the needle increases its temperature and pressure rapidly. This condition is called "vapor lock." Since the liquid and vapor phases are identical in their molar volume, and hence cooling power at the critical point, the cooling system at or above the critical point can never vapor lock. But for conditions slightly below the critical below the critical point, the needle may avoid vapor lock as well.

Embodiments of the invention avoid the occurrence of vapor lock and permit decreased probe sizes by operating in cryogen pressure-temperature regimes that avoid any crossing of the liquid-gas phase line. In particular embodiments, cryogenic cooling is achieved by operating near the critical point for the cryogen. When operating in this region, heat flows into the near-critical cryogen from the surrounding environment since the critical-point temperature (e.g., −147° C. in the case of $N_2$) is much colder that the surrounding environment. This heat is removed by the flow of the near critical cryogen through the tip of a cryoprobe, even though there is no latent heat of evaporation to assist with the cooling process. While the scope of the invention is intended to include operation in any regime having a pressure greater than the critical-point pressure, the cooling efficiency tends to decrease as the pressure is increased above the critical pressure. This is a consequence of increasing energy requirements needed to achieve flow at higher operating pressures.

Cryoablation Systems

Figure 2A:
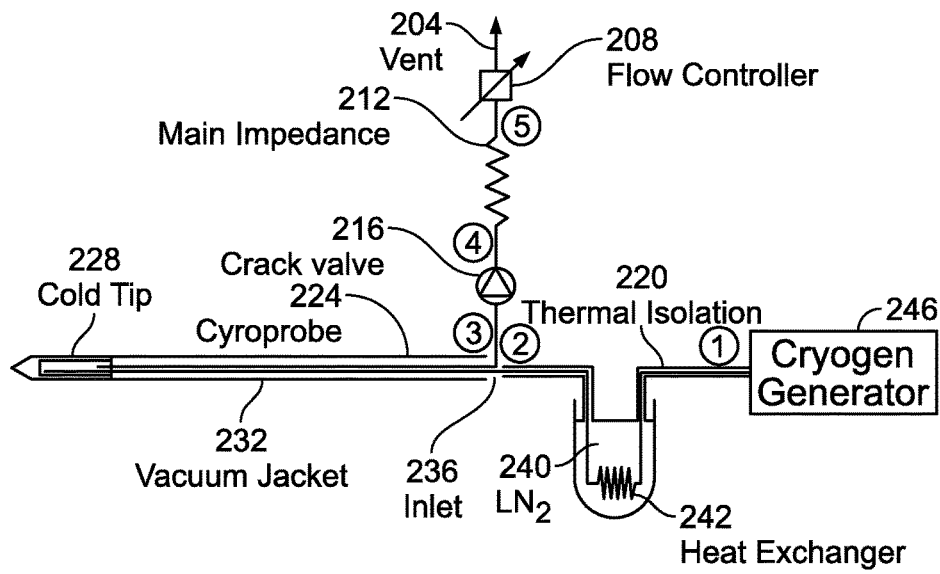
FIG. 2A is a schematic illustration of a cryogenic cooling system.
Figure 2B:
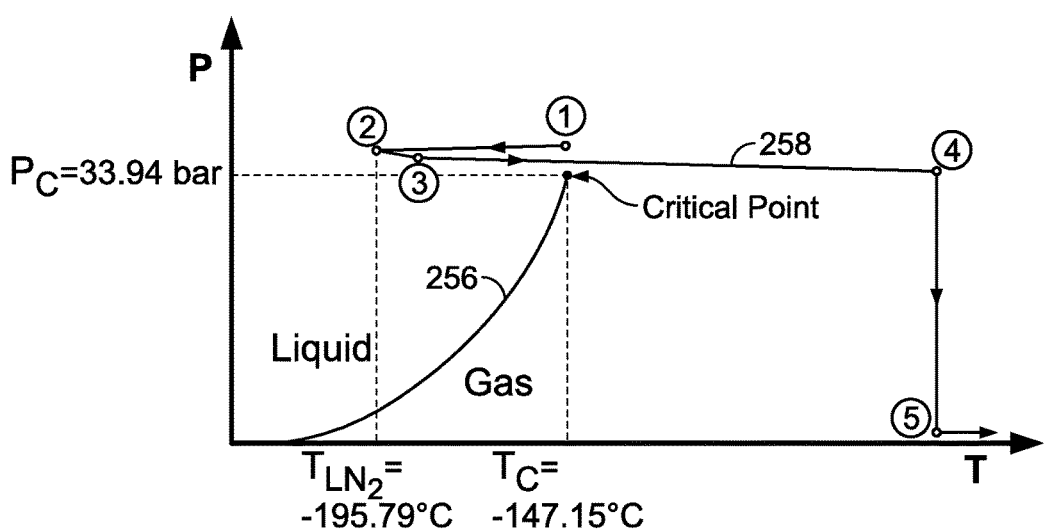
FIG. 2B is a cryogen phase diagram to illustrate a method for cryogenic cooling.

FIG. 2A provides a schematic illustration of a structural arrangement for a cryogenic system in one embodiment, and FIG. 2B provides a phase diagram that illustrates a thermodynamic path taken by the cryogen when the system of FIG. 2A is operated. The circled numerical identifiers in the two figures correspond so that a physical position is indicated in FIG. 2A where operating points identified along the thermodynamic path are achieved. The following description thus sometimes makes simultaneous reference to both the structural drawing of FIG. 2A and to the phase diagram of FIG. 2B in describing physical and thermodynamic aspects of the cooling flow. For purposes of illustration, both FIGS. 2A and 2B make specific reference to a nitrogen cryogen, but this is not intended to be limiting. The invention may more generally be used with any suitable cryogen, as will be understood by those of skill in the art; merely by way of example, alternative cryogens that may be used include argon, helium, hydrogen, and oxygen. In FIG. 2B, the liquid-gas phase line is identified with reference label 256 and the thermodynamic path followed by the cryogen is identified with reference label 258.

A cryogenic generator 246 is used to supply the cryogen at a pressure that exceeds the critical-point pressure $P_c$ for the cryogen at its outlet, referenced in FIGS. 2A and 2B by label {circle around (1)}. The cooling cycle may generally begin at any point in the phase diagram having a pressure above or slightly below $P_c$, although it is advantageous for the pressure to be near the critical-point pressure P. The cooling efficiency of the process described herein is generally greater when the initial pressure is near the critical-point pressure $P_c$ so that at higher pressures there may be increased energy requirements to achieve the desired flow. Thus, embodiments may sometimes incorporate various higher upper boundary pressure but generally begin near the critical point, such as between 0.8 and 1.2 times $P_c$, and in one embodiment at about 0.85 times $P_c$.

As used herein, the term "near critical" refers to near the liquid-vapor critical point. Use of this term is equivalent to "near a critical point" and it is the region where the liquid-vapor system is adequately close to the critical point, where the dynamic viscosity of the fluid is close to that of a normal gas and much less than that of the liquid; yet, at the same time its density is close to that of a normal liquid state. The thermal capacity of the near critical fluid is even greater than that of its liquid phase. The combination of gas-like viscosity, liquid-like density and very large thermal capacity makes it a very efficient cooling agent. In other words, reference to a near critical point refers to the region where the liquid-vapor system is adequately close to the critical point so that the fluctuations of the liquid and vapor phases are large enough to create a large enhancement of the heat capacity over its background value. The near critical temperature is a temperature within ±10% of the critical point temperature. The near critical pressure is between 0.8 and 1.2 times the critical point pressure.

Referring again to FIG. 2A, the cryogen is flowed through a tube, at least part of which is surrounded by a reservoir 240 of the cryogen in a liquid state, reducing its temperature without substantially changing its pressure. In FIG. 2A, reservoir is shown as liquid $N_2$, with a heat exchanger 242 provided within the reservoir 240 to extract heat from the flowing cryogen. Outside the reservoir 240, thermal insulation 220 may be provided around the tube to prevent unwanted warming of the cryogen as it is flowed from the cryogen generator 246. At point 2, where the temperature is at $T_{LN2}$, after being cooled by being brought into thermal contact with the liquid cryogen, the cryogen has a lower temperature but is at substantially the initial pressure. In some instances, there may be a pressure change, as is indicated in FIG. 2B in the form of a slight pressure decrease, provided that the pressure does not drop substantially below the critical-point pressure $P_c$, i.e. does not drop below the determined minimum pressure. In the example shown in FIG. 2B, the temperature drop as a result of flowing through the liquid cryogen is about 47° C.

The cryogen is then provided to a device for use in cryogenic applications. In the exemplary embodiment shown in FIG. 2A, the cryogen is provided to an inlet 236 of a cryoprobe 224, such as may be used in medical cryogenic applications, but this is not a requirement.

In embodiments, the cryogen may be introduced through a proximal portion of a catheter, along a flexible intermediate section of the catheter, and into the distal treatment section of the catheter. At the point when the cryogen is provided to such treatment region of the device, indicated by labels 2 and 3 in FIGS. 2A and 2B, there may be a slight change in pressure and/or temperature of the cryogen as it moves through an interface with the device, i.e. such as when it is provided from the tube to the cryoprobe inlet 236 in FIG. 2A. Such changes may typically show a slight increase in temperature and a slight decrease in pressure. Provided the cryogen pressure remains above the determined minimum pressure (and associated conditions), slight increases in temperature do not significantly affect performance because the cryogen simply moves back towards the critical point without encountering the liquid-gas phase line 256, thereby avoiding vapor lock.

Thermal insulation along the shaft of the cryotherapy apparatus (e.g., needles), and along the support system that delivers near-critical freeze capability to these needles, may use a vacuum of better than one part per million of atmospheric pressure. Such a vacuum may not be achieved by conventional two-stage roughing pumps alone. The percutaneous cryotherapy system in an embodiment thus incorporates a simplified method of absorption pumping rather than using expensive and maintenance-intensive high-vacuum pumps, such as diffusion pumps or turbomolecular pumps. This may be done on an internal system reservoir of charcoal, as well as being built into each individual disposable probe.

Embodiments incorporate a method of absorption pumping in which the liquid nitrogen bath that is used to sub-cool the stream of incoming nitrogen near its critical point is also used to cool a small volume of clean charcoal. The vast surface area of the charcoal permits it to absorb most residual gas atoms, thus lowering the ambient pressure within its volume to well below the vacuum that is used to thermally insulate the needle shaft and the associated support hardware. This volume that contains the cold charcoal is attached through small-diameter tubing to the space that insulates the near-critical cryogen flow to the needles. Depending upon the system design requirements for each clinical use, the charcoal may be incorporated into the cooling reservoir of liquid cryogen 240 seen in FIG. 2A, or become part of the cryoprobe 224, near the connection of the extension hose near the inlet 236. Attachments may be made through a thermal contraction bayonet mount to the vacuum space between the outer shaft of the vacuum jacketed needles and the internal capillaries that carry the near-critical cryogen, and which is thermally insulated from the surrounding tissue. In this manner, the scalability of the system extends from simple design constructions, whereby the charcoal-vacuum concept may be incorporated into smaller reservoirs where it may be more convenient to draw the vacuum. Alternatively, it may be desirable for multiple-probe systems to individually incorporate small charcoal packages into each cryoprobe near the junction of the extension hose/cryoprobe with the machine interface, such that each hose and cryoprobe draws its own vacuum, thereby further reducing construction costs.

Flow of the cryogen from the cryogen generator 246 through the cryoprobe 224 or other device may be controlled in the illustrated embodiment with an assembly that includes a crack valve 216, a main impedance 212, and a flow controller. The cryoprobe 224 itself may comprise a vacuum jacket 232 along its length and may have a cold tip 228 that is used for the cryogenic applications. Unlike a Joule-Thomson probe, where the pressure of the working cryogen changes significantly at the probe tip, these embodiments of the invention provide relatively little change in pressure throughout the probe. Thus, at point 4, the temperature of the cryogen has increased approximately to ambient temperature, but the pressure remains elevated. By maintaining the pressure above the critical-point pressure $P_c$ throughout the process, the liquid-gas phase line 256 is never encountered along the thermodynamic path 258 and vapor lock is thereby avoided. The cryogen pressure returns to ambient pressure at point 5 before passing through the flow controller 208, which is typically located well away from the cryoprobe 224. The cryogen may then be vented through vent 204 at substantially ambient conditions. See also U.S. Pat. No. 8,387,402 to Littrup et al. for arrangements of near critical fluid cryoablation systems.

Figure 3:
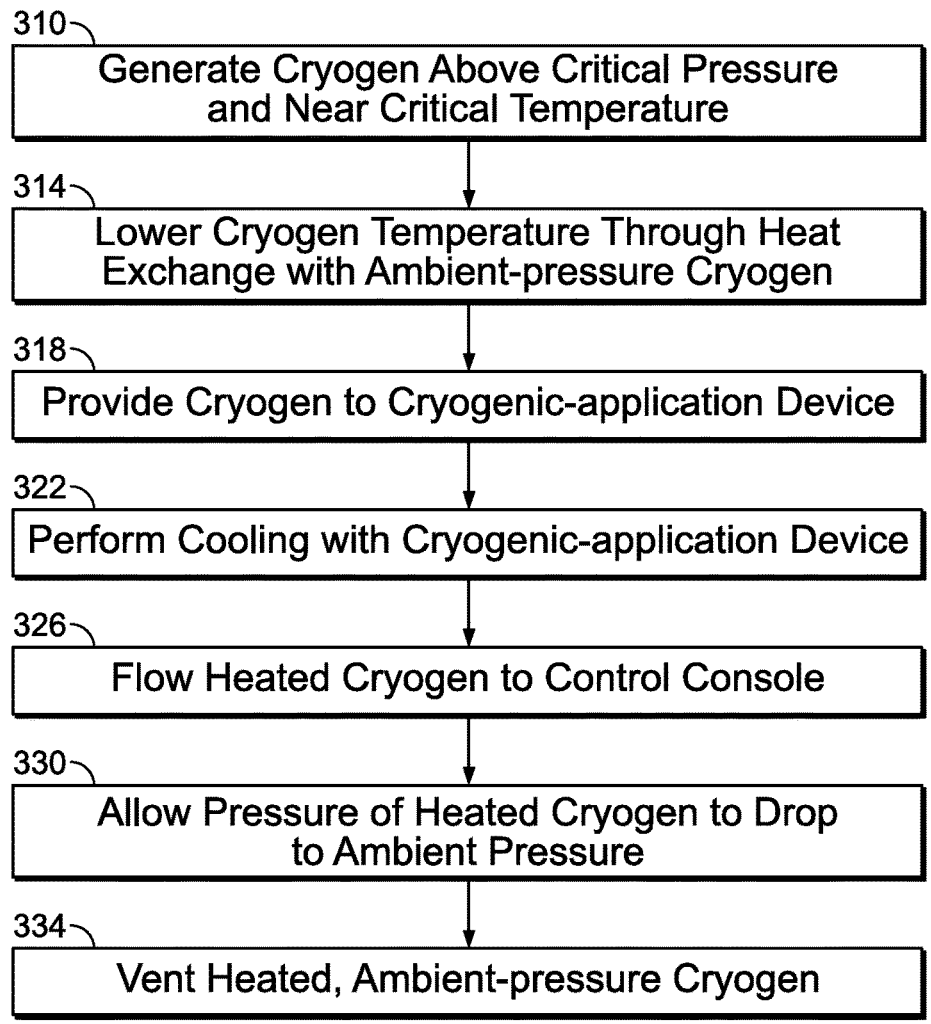
FIG. 3 is a flow diagram of the cooling method of FIG. 2A.

A method for cooling in one embodiment in which the cryogen follows the thermodynamic path shown in FIG. 2B is illustrated with the flow diagram of FIG. 3. At block 310, the cryogen is generated with a pressure that exceeds the critical-point pressure and is near the critical-point temperature. The temperature of the generated cryogen is lowered at block 314 through heat exchange with a substance having a lower temperature. In some instances, this may conveniently be performed by using heat exchange with an ambient-pressure liquid state of the cryogen, although the heat exchange may be performed under other conditions in different embodiments. For instance, a different cryogen might be used in some embodiments, such as by providing heat exchange with liquid nitrogen when the working fluid is argon. Also, in other alternative embodiments, heat exchange may be performed with a cryogen that is at a pressure that differs from ambient pressure, such as by providing the cryogen at lower pressure to create a colder ambient.

The further cooled cryogen is provided at block 318 to a cryogenic-application device, which may be used for a cooling application at block 322. The cooling application may comprise chilling and/or freezing, depending on whether an object is frozen with the cooling application. The temperature of the cryogen is increased as a result of the cryogen application, and the heated cryogen is flowed to a control console at block 326. While there may be some variation, the cryogen pressure is generally maintained greater than the critical-point pressure throughout blocks 310-326; the principal change in thermodynamic properties of the cryogen at these stages is its temperature. At block 330, the pressure of the heated cryogen is then allowed to drop to ambient pressure so that the cryogen may be vented, or recycled, at block 334. In other embodiments, the remaining pressurized cryogen at block 326 may also return along a path to block 310 to recycle rather than vent the cryogen at ambient pressure.

Cryogen Generators

Figure 4:
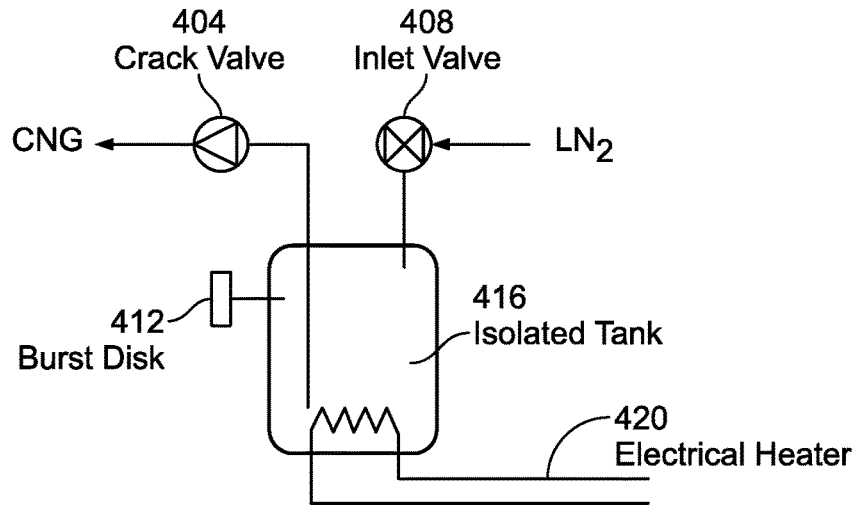
FIG. 4 is a schematic illustration of a cryogenic generator.

There are a variety of different designs that may be used for the cryogen source or generator 246 in providing cryogen at a pressure that exceeds the critical-point pressure, or meets the near-critical flow criteria, to provide substantially uninterrupted cryogen flow at a pressure and temperature near its critical point. In describing examples of such designs, nitrogen is again discussed for purposes of illustration, it being understood that alternative cryogens may be used in various alternative embodiments. FIG. 4 provides a schematic illustration of a structure that may be used in one embodiment for the cryogen generator. A thermally insulated tank 416 has an inlet valve 408 that may be opened to fill the tank 416 with ambient liquid cryogen ($LN_2$). A resistive heating element 420 is located within the tank 416, such as in a bottom section of the tank 416, and is used to heat the cryogen when the inlet valve is closed. Heat is applied until the desired operating point is achieved, i.e. at a pressure that exceeds the near-critical flow criteria. A crack valve 404 is attached to an outlet of the tank 416 and set to open at the desired pressure. In one embodiment that uses nitrogen as a cryogen, for instance, the crack valve 404 is set to open at a pressure of about 33.9 bar, about 1 bar greater than the critical-point pressure. Once the crack valve 404 opens, a flow of cryogen (CNG) is supplied to the system as described in connection with FIGS. 2A and 2B above.

A burst disk 412 may also be provided consistent with safe engineering practices to accommodate the high cryogen pressures that may be generated. The extent of safety components may also depend in part on what cryogen is to be used since they have different critical points. In some instances, a greater number of burst disks and/or check valves may be installed to relieve pressures before they reach design limits of the tank 416 in the event that runaway processes develop.

During typical operation of the cryogen generator, an electronic feedback controller maintains current through the resistive heater 420 to a level sufficient to produce a desired flow rate of high-pressure cryogen into the system. The actual flow of the cryogen out of the system may be controlled by a mechanical flow controller 208 at the end of the flow path as indicated in connection with FIG. 2A. The amount of heat energy needed to reach the desired cryogen pressures is typically constant once the inlet valve 408 has been closed. The power dissipated in the resistive heater 420 may then be adjusted to keep positive control on the mechanical flow controller 208. In an alternative embodiment, the mechanical flow controller 208 is replaced with the heater controller for the cryogen generator. In such an embodiment, once the crack valve 404 opens and high-pressure cryogen is delivered to the rest of the system, the feedback controller continuously adjusts the current through the resistive heater to maintain a desired rate of flow of gaseous cryogen out of the system. The feedback controller may thus comprise a computational element to which the heater current supply and flow controller are interfaced.

Flexible Multi-Tubular Cryoablation Catheter

FIGS. 5 and 6 illustrate a flexible multi-tubular cryoprobe 10. The cryoprobe 10 includes a housing 12 for receiving an inlet flow of near critical cryogenic fluid from a fluid source (not shown) and for discharging an outlet flow of the cryogenic fluid. A plurality of fluid transfer tubes 14, 14' are securely attached to the housing 12. These tubes include a set of inlet fluid transfer tubes 14 for receiving the inlet flow from the housing; and, a set of outlet fluid transfer tubes 14' for discharging the outlet flow to the housing 12. Each of the fluid transfer tubes 14, 14' is formed of material that maintains flexibility in a full range of temperatures from −200° C. to ambient temperature. Each fluid transfer tube has an inside diameter in a range of between about 0.10 mm and 1.0 mm (preferably between about 0.20 mm and 0.50 mm). Each fluid transfer tube has a wall thickness in a range of between about 0.01 mm and 0.30 mm (preferably between about 0.02 mm and 0.10 mm). An end cap 16 is positioned at the ends of the fluid transfer tubes 14, 14' to provide fluid transfer from the inlet fluid transfer tubes 14 to the outlet fluid transfer tubes 14'.

In embodiments the tubes 14, 14' are formed of annealed stainless steel or a polyimide, preferably Kapton® polyimide. These materials maintain flexibility at a near critical temperature. By flexibility, it is meant the ability of the cryoprobe to be bent in the orientation desired by the user without applying excess force and without fracturing or resulting in significant performance degradation.

The cryogenic fluid utilized is preferably near critical nitrogen. However, other fluids may be utilized such as argon, neon, helium or others.

The fluid source for the cryogenic fluid may be provided from a suitable mechanical pump or a non-mechanical critical cryogen generator as described above. Such fluid sources are disclosed in, for example, U.S. patent application Ser. No. 10/757,768 which issued as U.S. Pat. No. 7,410,484, on Aug. 12, 2008 entitled "CRYOTHERAPY PROBE", filed Jan. 14, 2004 by Peter J. Littrup et al.; U.S. patent application Ser. No. 10/757,769 which issued as U.S. Pat. No. 7,083,612 on Aug. 1, 2006, entitled "CRYOTHERAPY SYSTEM", filed Jan. 14, 2004 by Peter J. Littrup et al.; U.S. patent application Ser. No. 10/952,531 which issued as U.S. Pat. No. 7,273,479 on Sep. 25, 2007 entitled "METHODS AND SYSTEMS FOR CRYOGENIC COOLING" filed Sep. 27, 2004 by Peter J. Littrup et al. U.S. Pat. Nos. 7,410,484, 7,083,612 and 7,273,479 are incorporated herein by reference, in their entireties, for all purposes.

The endcap 16 may be any suitable element for providing fluid transfer from the inlet fluid transfer tubes to the outlet fluid transfer tubes. For example, endcap 16 may define an internal chamber, cavity, or passage serving to fluidly connect tubes 14, 14'.

There are many configurations for tube arrangements. In one class of embodiments the tubes are formed of a circular array, wherein the set of inlet fluid transfer tubes comprises at least one inlet fluid transfer tube defining a central region of a circle and wherein the set of outlet fluid transfer tubes comprises a plurality of outlet fluid transfer tubes spaced about the central region in a circular pattern. In the configuration shown in FIG. 6, the tubes 14, 14' fall within this class of embodiments.

During operation, the cryogen fluid arrives at the cryoprobe through a supply line from a suitable nitrogen source at a temperature close to −200° C., is circulated through the multi-tubular freezing zone provided by the exposed fluid transfer tubes, and returns to the housing.

In embodiments, the nitrogen flow does not form gaseous bubbles inside the small diameter tubes under any heat load, so as to not create a vapor lock that limits the flow and the cooling power. By operating at the near critical condition the vapor lock is eliminated as the distinction between the liquid and gaseous phases disappears.

Embodiments of the present invention provides a substantial increase in the heat exchange area between the cryogen and tissue, over prior art cryoprobes, by this multi-tubular design. Depending on the number of tubes used, the present cryoprobes can increase the contact area several times over previous cryoprobes having similarly sized diameters with single shafts.

Figure 7:
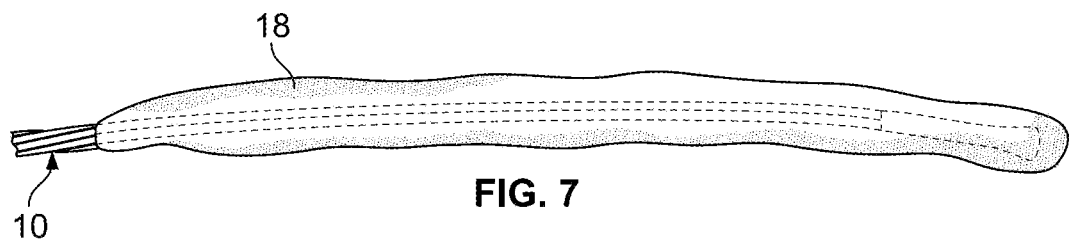
FIG. 7 is a perspective view of cryoprobe of FIG. 5 operated to generate an iceball.
Figure 8:
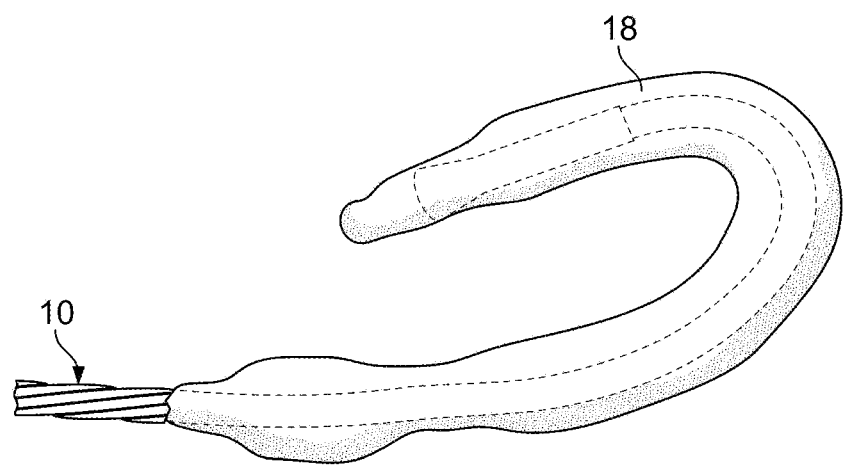
FIG. 8 is a perspective view of the cryoprobe of FIG. 5 that is bent to approximately 180° to form a commensurately bent iceball.
Figure 9:
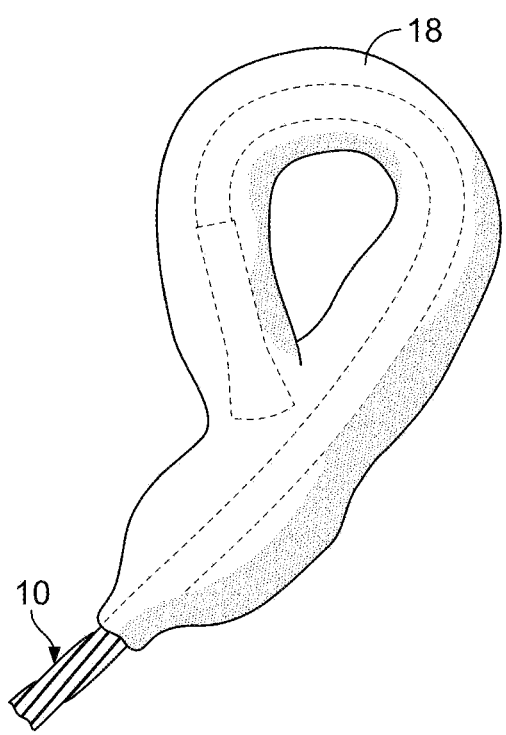
FIG. 9 illustrates the cryoprobe sufficiently bent so as to form a loop.

As can be seen in FIG. 7, an iceball 18 is generated about the cryoprobe 10. Referring now to FIG. 8, it can be seen that an iceball 18 can be created in the desired shape by bending or articulating the cryoprobe in the desired orientation. A complete iceball 18 loop can be formed, as shown in FIG. 9.

Figures 10, 11:
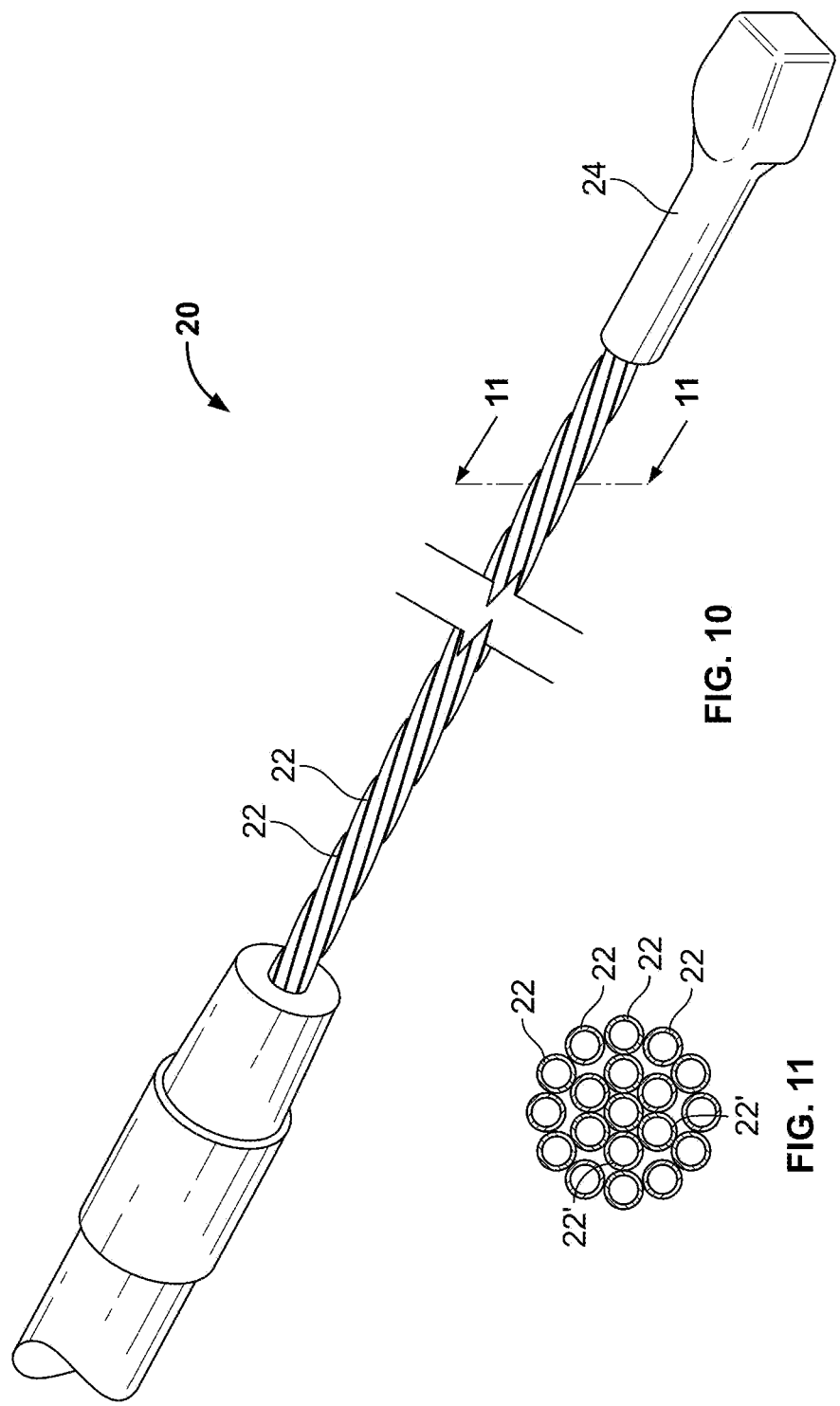
FIG. 10 is a perspective view of another cryoprobe having a flexible distal section.
FIG. 11 is a view taken along line 11-11 of FIG. 10.

Referring now to FIG. 10, a cryoprobe 20 is illustrated, which is similar to the embodiment of FIG. 5, however, with this embodiment a polyimide material is used to form the tubes 22, 22'. Furthermore, this figure illustrates the use of a clamp 24 as an endcap. Although polyimide tubing is described to achieve flexibility and conformability to target structures, in other embodiments, as described further herein, the catheter may incorporate memory or shape set components to cause predetermined bends. Additionally, pull wires, actuators, and spine elements may be added to the distal section to create desirable bends and shapes.

Referring now to FIG. 12, one embodiment of the housing 12 of a cryoprobe 10 is illustrated. The housing 12 includes a handle 26 that supports an inlet shaft 28 and an outlet shaft 30. The inlet shaft 28 is supported within the handle 26 for containing proximal portions of the set of inlet fluid transfer tubes 32. The outlet shaft 30 is supported within the handle 26 for containing proximal portions of the set of outlet fluid transfer tubes 34. Both of the shafts 28, 30 include some type of thermal insulation, preferably a vacuum, to isolate them.

Referring now to FIGS. 13-15 various configurations of tube configurations are illustrated. In FIG. 13 a configuration is illustrated in which twelve inlet fluid transfer tubes 36 circumscribe a single relatively large outlet fluid transfer tube 36'. In FIG. 14, three inlet fluid transfer tubes 38 are utilized with four outlet fluid transfer tubes 38'. In FIG. 15, a plane of inlet fluid transfer tubes 40 are formed adjacent to a plane of outlet of fluid transfer tubes 40'.

In an example, an annealed stainless steel cryoprobe was utilized with twelve fluid transfer tubes. There were six inlet fluid transfer tubes in the outer circumference and six outlet fluid transfer tubes in the center. The tubes were braided as shown in FIG. 5. The length of the freeze zone was 6.5 inches. Each fluid transfer tube had an outside diameter of 0.16 inch and an inside diameter 0.010 inch. The diameter of the resultant array of tubes was 0.075 inch. After a one minute freeze in 22° C. water and near-critical (500 psig) nitrogen flow of approximately 20 STP l/min, ice covered the entire freeze zone of the flexible cryoprobe with an average diameter of about 0.55 inch. After four minutes the diameter was close to 0.8 inch. The warm cryoprobe could be easily bent to any shape including a full loop of approximately 2 inch in diameter without any noticeable change in its cooling power.

In another example, a polyimide cryoprobe was utilized with twenty-one fluid transfer tubes. There were ten inlet fluid transfer tubes in the outer circumference and eleven outlet fluid transfer tubes in the center. The tubes were braided. The length of the freeze zone was 6.0 inches. Each fluid transfer tube had an outside diameter of 0.0104 inch and an inside diameter 0.0085 inch. Each tube was pressure rated for about 1900 psig (working pressure 500 psig). The average diameter of the flexible portion of the cryoprobe was 1.15 mm (0.045 inch). The cryoprobe was extremely flexible with no perceivable "memory" in it. It bent by its own weight of just 1 gram and easily assumed any shape with a bending radius as little as 0.1 inch, including a 1 inch diameter "knot". A full loop was created with the cryoprobe. After a one minute freeze in 22° C. water and near critical (500 psig) nitrogen flow of approximately 20 STP l/min, ice covered the entire freeze zone of the flexible cryoprobe with an average diameter of 0.65 inch and in two minutes it closed the entire 1 inch hole inside the loop. See also, U.S. Publication No. 2011/0040297 to Babkin et al. for additional cryoprobe and catheter designs.

Cryoablation Catheter with Spring-Biased Distal Treatment Section

Figure 16:
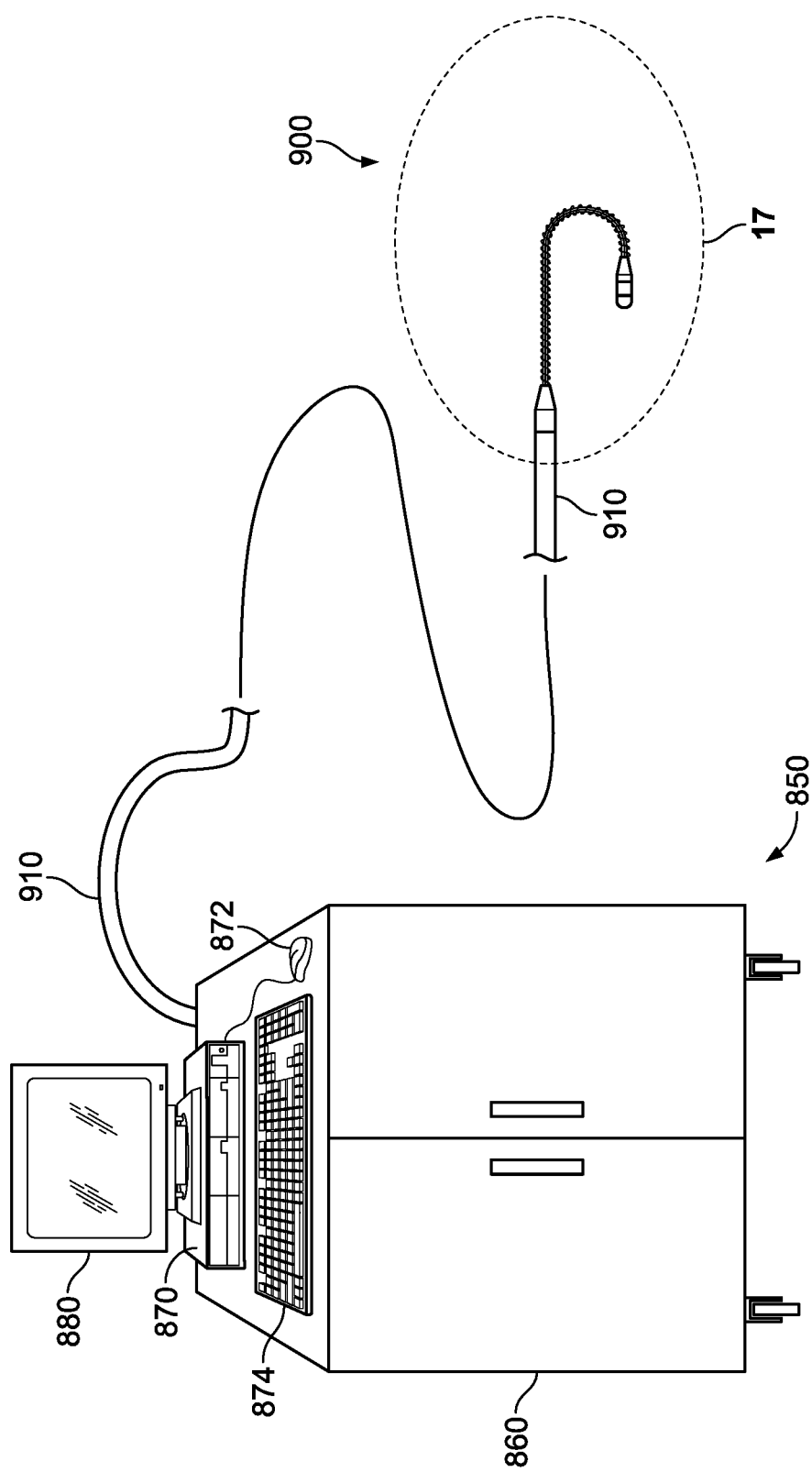
FIG. 16 is an illustration of a cryoablation system including a cryoablation catheter.

FIG. 16 illustrates a cryoablation system 850 having a cart or console 860 and a cryoablation catheter 900 detachably connected to the console via a flexible elongate tube 910. The cryoablation catheter 900, which shall be described in more detail below in connection with FIG. 17, includes a spring biased distal treatment section which serves to match the contour of a target anatomical region.

The console 860 may include a variety of components (not shown) such as, for example, a generator, controller, tank, valve, pump, etc. A computer 870 and display 880 are shown in FIG. 16 positioned on top of cart for convenient user operation. Computer may include a controller, or communicate with an external controller to drive components of the cryoablation systems such as a pump, valve or generator.

Input devices such as a mouse 872 and a keyboard 874 may be provided to allow the user to input data and control the cryoablation devices.

In embodiments computer 870 is configured or programmed to control cryogen flowrate, pressure, and temperatures as described herein. Target values and real time measurement may be sent to, and shown, on the display 880.

Figure 17:
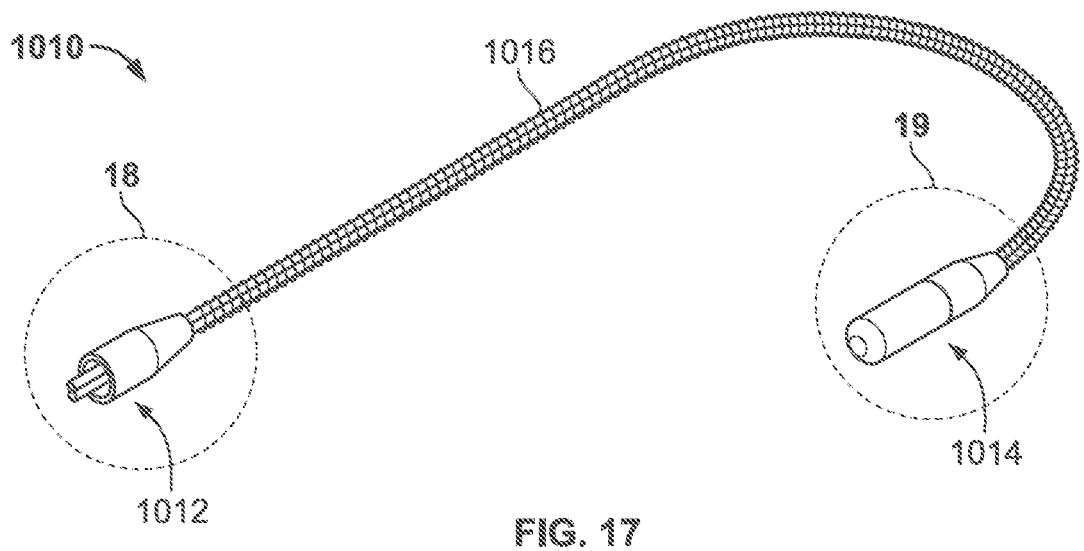
FIG. 17 is an enlarged view of the curved distal treatment section shown in FIG. 16.

With reference to FIG. 17 the distal treatment section 1010 is shown in a deflected or curved configuration and includes a proximal end 1012, a distal tip 1014, and treatment or freeze zone 1016 therebetween. As will be described in more detail herein, the curvature of the treatment section may be controlled to match a particular anatomy such as the interior surface of the heart.

Figure 18:
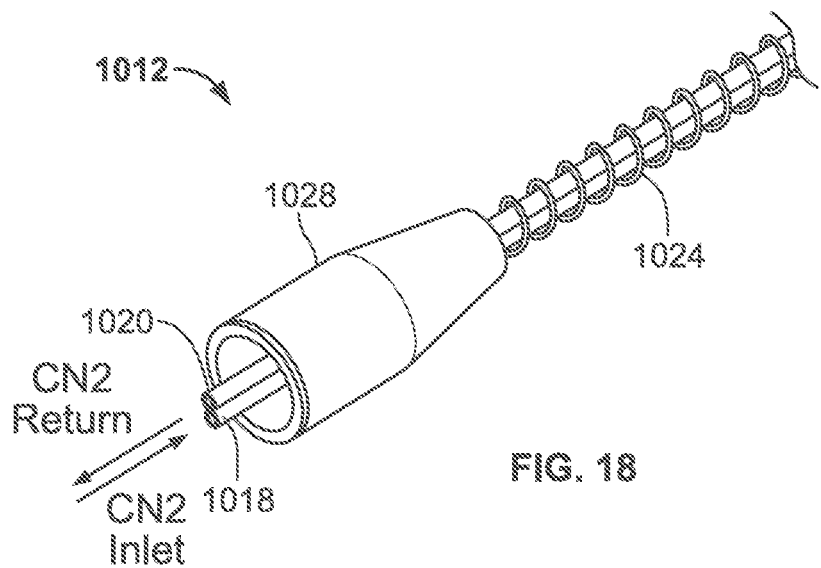
FIG. 18 is an enlarged view of the proximal end of the distal treatment section shown in FIG. 17.
Figure 19:
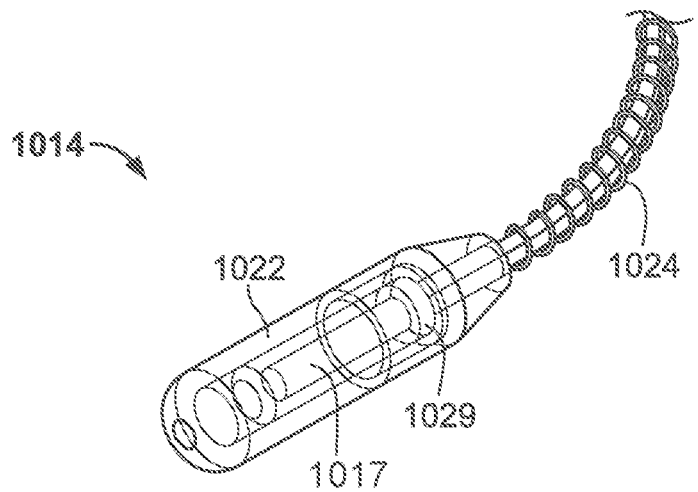
FIG. 19 is an enlarged view of the distal tip of the distal treatment section shown in FIG. 17.

With reference to FIGS. 18 and 19 which show enlarged views of the proximal end 1012 and the distal end 1014 respectively, at least one fluid delivery tube 1018 extends through the distal treatment section to a chamber or cavity 1017 in the distal tip. A fluid return tube 1020 extends through the distal treatment section from the chamber 1017 to transport the cooling fluid from the chamber to a storage tank or exhaust structure as desired. As described herein, a cooling fluid may be transported from a fluid source, through an intermediate section of the catheter or apparatus, and through the tube bundle in order to freeze the target tissue placed in contact with the distal treatment section 1016.

The fluid ($CN_2$) transport tubes 1018,1020 in the treatment section are preferably made of a material adapted to safely hold fluids under pressure 2-3 times the working pressure. Consequently, secondary or redundant outer balloons/covers are unnecessary. Additionally, the tubes are desirably good thermal conductors in order to transfer heat from the tissue to the fluid. The fluid transport tubes 1018, 1020 preferably have an outer diameter ranging from 0.2 to 2 mm. The fluid transport tubes are shown being smooth, and without corrugations or grooves. However, in embodiments, the structures may include textures, ridges, and corrugations.

Additionally, in embodiments, the tubes are preferably made of materials that have a preset shape as described further herein. An exemplary material is a shape memory metal or alloy (e.g., Nitinol). However, other materials may be suitable including various polymers, stainless steels, spring steel, etc.

Attachment of the distal tip section to the body or intermediate section of the cryoablation catheter may be carried out as described herein and include, for example, a seal or transition hub 1028 which engages the outside of the intermediate section of the catheter (not shown). For example, with reference to FIG. 16, a hub may be joined to inlet line of system 850. Glues, adhesives, and shrink tube sleeves may be incorporated into the designs to hold the components together. Insulation layers including an air or vacuum gap may be incorporated into the intermediate section of the catheter as described herein.

With reference to FIG. 19, the distal tip 1014 may include a seal and adhesive layers to secure the chamber to the plurality of transport tubes and to prevent leaks. The cap may include a redundant or double seals. For example, a second cap 1022 may be situated or encapsulate a first cap 1029. In this manner, a cooling liquid under the pressures described herein may be safely transported to and from the distal tip without the danger of a leak.

FIGS. 18-19 also show a tubular member 1024 surrounding the transport tubes. The tubular member 1024 maintains the transport tube bundle together when the treatment section is articulated or bends. The tubular member 1024 shown in this embodiment also allows tissue and bodily fluids to contact the transport tubes directly thereby increasing thermal conductivity between the cooling fluid and the target tissue. Although the tubular member 1024 is shown as a coil in this embodiment, the invention is not so limited and the coil need not be present. Alternative structures may be utilized to hold the tube bundle together so that it may actuated as a unit. Examples include tacking structures, welds, adhesives, two or more spot welds, and bands. Alternatively, tube elements may be coextruded or formed to operate as an integrated articulatable member.

Figure 20:
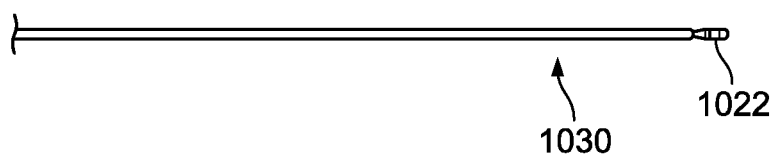
FIGS. 20-23 are illustrations of a distal treatment section being deployed from a first configuration to a second configuration.

FIGS. 20-23 show a distal treatment section 1016 of a cryoablation catheter being deployed. With reference to FIG. 20, an outer sheath or sleeve 1030 is shown. It surrounds a plurality of tube members. The tubes are made of a shape memory alloy in this embodiment. The outer sheath 1030 holds or constrains the transport tubes, preventing the transport tubes from assuming a preset shape. The outer sheath is desirable flexible enough to be navigated through the vasculature, or through a guide catheter already positioned in the vasculature, but rigid enough to retrain the shape member tubes in an undeployed configuration. Exemplary materials for the outer sheath or sleeve include polymers such as, the polymers and materials used in endovascular applications. Non-limiting examples include polyethylene (PE), polypropylene (PP), polyvinyl chloride (PVC) and fluorocarbons (PTFE).

Upon reaching the destination or target tissue (not shown), the sheath 1030 and treatment section 1016 are moved relative to one another such that the distal treatment section projects from the end of the sheath. For example, the sheath may be retracted (R) by manipulating the sheath by hand at the proximal end of the catheter, or more sophisticated structures may be incorporated such as thumb pad or lever as described in U.S. Pat. No. 6,984,230 to Scheller et al.

Figure 21:
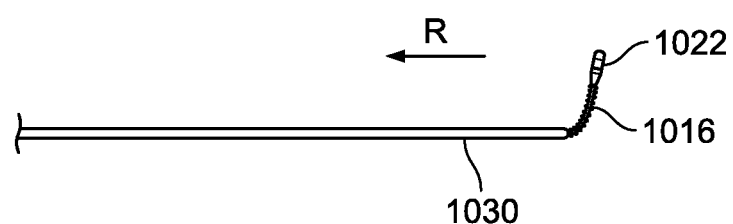

With reference to FIG. 21, the tip 1022 is shown immediately curving as it extends from the sheath to an offset position. A diagnostic or imaging modality may be employed such as fluoroscopy to confirm location and deployment of the distal treatment section. Radio-opaque bands or markers may be carried on the distal treatment section 1016 (not shown) to facilitate location and visualization of the device in situ.

Figure 22:
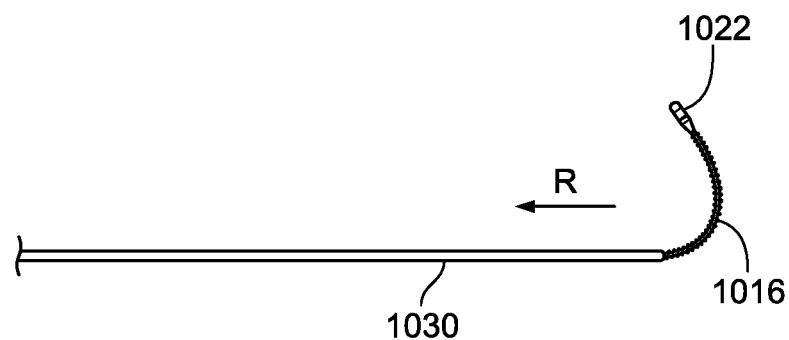

FIG. 22 shows distal treatment section 1016 being further deployed from sheath 1030. Treatment section 1016 continues to assume its preset shape.

Figure 23:
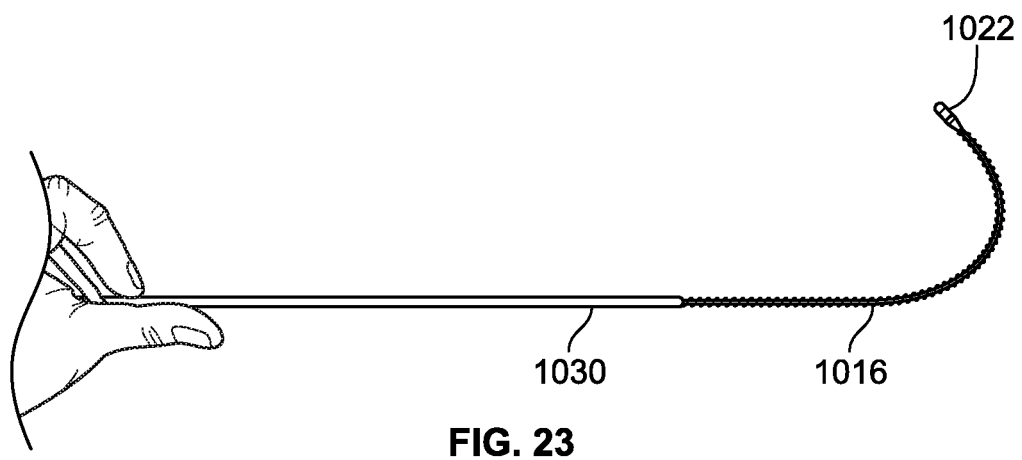
Figure 24:
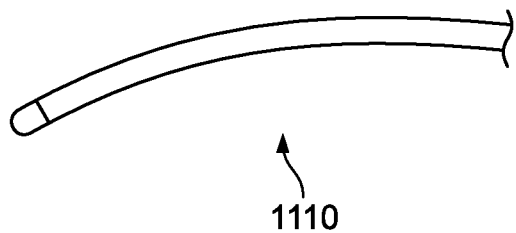
FIGS. 24-27 are illustrations of a distal treatment section being deployed from a constrained state, to a plurality of different shapes.

FIG. 23 shows distal treatment section 1016 fully deployed. The curved configuration shown in FIG. 23 is, for example, a predetermined deflection to match an anatomy of a target tissue. Exemplary tissues and targets to be treated include myocardial tissue including without limitation the myocardial tissue of the left or right atrium. However, the shape of the curve or deflection in the second configuration may vary widely and the physician may manipulate the shape by controlling the degree of deployment, or selecting a different preset shape to match a particular anatomy or target area.

In embodiments a cryoablation method comprises providing a cryoablation catheter including a distal treatment section. The distal treatment section is positioned in the vicinity of the target tissue. The distal treatment section is partially deployed, namely, the sheath is retracted, allowing the distal treatment section to partially deflect into its preset shape. The location of the tip and distal treatment section are confirmed to be in proper position relative to the anatomy and target tissue to be ablated.

Upon confirmation of the location of the distal treatment section, it is further deployed or released until the distal treatment section is fully deployed and in proper position relative to the target tissue. Preferably the treatment section or freeze zone is contacting the segment of tissue to be ablated. Optionally, the position is reconfirmed. Then, the catheter is activated to cause the treatment section to stick to the tissue, locking its position in place. Cooling power is continued until the target tissue/lesion has been sufficiently ablated. For example, as discussed further herein, in the case of treating atrial fibrillation, a full thickness or transmural linear lesion may be effected. The cooling power is then halted to allow the distal treatment section to thaw, and de-stick from the tissue. The distal treatment section may then be retracted within the outer sheath, and the catheter removed from the target area. In embodiments a controller measures temperature, flow rate, and time elapsed, and halts the cooling power once a threshold condition is reached. In embodiments, the cooling power is halted after a time period has elapsed.

Figure 25:
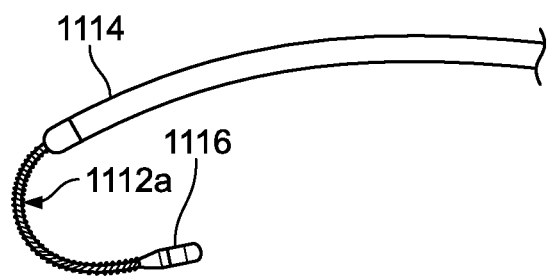
Figure 26:
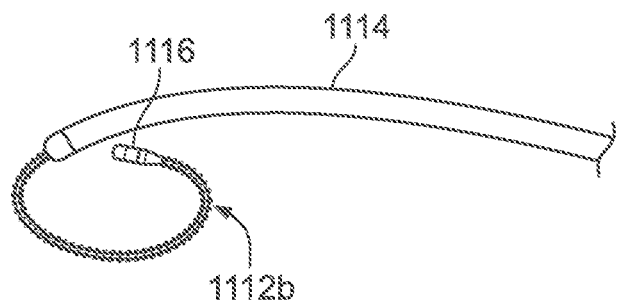
Figure 27:
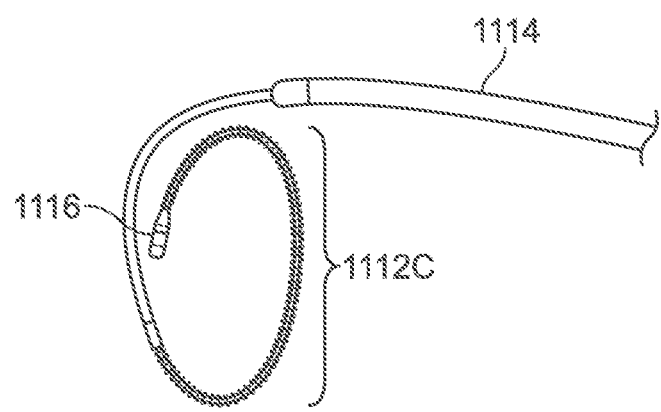

FIGS. 24-27 show another cryoablation catheter 1110 similar to that described in connection with FIGS. 20-23 except the distal treatment section includes a plurality of preformed (or preset) treatment shapes. More specifically, FIG. 25 shows distal treatment section having a concave portion 1112a. FIG. 26 shows distal treatment section having a convex portion 1112b. FIG. 27 shows distal treatment section having a flat portion 1112c. The distal treatment section assumes one of the predetermined shapes based on the travel distance the tip 1116 is ejected from the outer sheath 1114.

The shape of the distal treatment section is thus conveniently changed by adjusting the travel distance that the tip is ejected from the outer sheath. In this embodiment, the distal treatment section utilizes the property of elasticity so that it may automatically return to (or assume) its preformed shape. This embodiment of the invention avoids plastic deformation and operates using a different principle than malleable elongate shafts which do not spring back to an original shape when unconstrained. As will be described in more detail herein, the shapes can be preset to treat a plurality of different anatomical regions.

Figure 28:
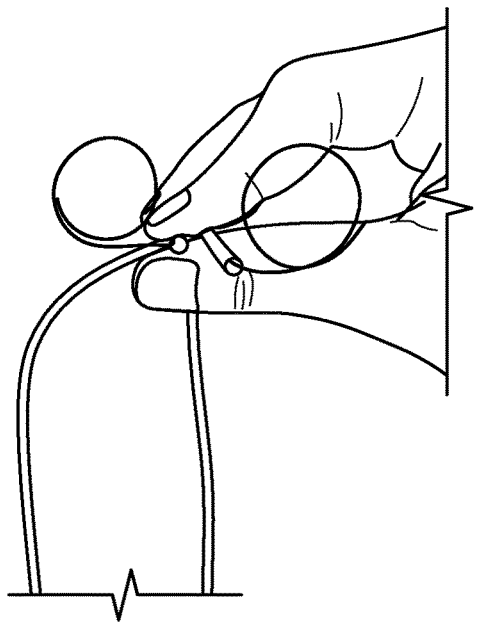
FIGS. 28-30 are illustrations of various distal deployed treatment sections having circular shapes.
Figure 29:
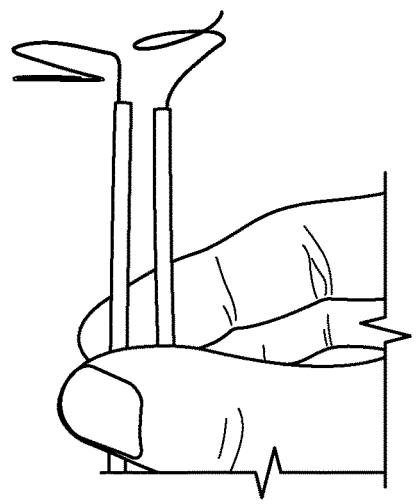
Figure 30:
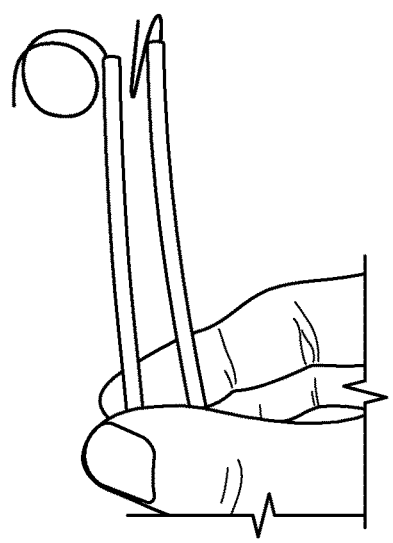

The preformed treatment shapes may have a wide variety of geometries. FIGS. 28-29, for example, show circular loops formed perpendicular to the axis of the sheath. FIG. 30 shows a circular loop formed substantially in the same plane as the axis of the sheath. Circular shapes may serve to treat circular-shaped anatomical regions such as the entries to the pulmonary vessels in connection with trying to eliminate atrial fibrillation.

Additionally, the plurality of different treatment shapes may have 1D, 2D or 3D configurations. One treatment shape may lie in the same plane as another treatment shape, i.e., coplanar. Alternatively, one treatment shape may lie outside the plane of another treatment shape.

The size of the preformed treatment shapes may vary. In embodiments the size and shape of the treatment section matches the anatomical surfaces in the heart. The size may be adjusted to suit different individuals.

The number of preformed treatment shapes per instrument may vary and be determined based on the target tissue or application. As described further herein, a treatment section having 1, 2 or 3 preset shapes may be desirable. However, a treatment section may be designed having 2-10 shapes, or perhaps 3-5 shapes, and in some embodiments only 3 preset shapes.

In other embodiments, a preformed stylus or preformed outer shell layer may be incorporated in the distal treatment section to create the above described preset shapes.

The preformed members may be shape set by wrapping or otherwise manipulating the member around a mandrel or mold. The entire fixture (mold and member) is then submerged in a temperature controlled bath for a sufficient time period to set the shape. In embodiments, the members exhibit superelastic properties. Examples of suitable shape set materials include without limitation Nitinol.

In yet another embodiment, a pull wire and optional spine element may be incorporated into the distal treatment section to articulate and deflect the treatment section to the desired curvature.

Applications

The ability to have a safe leak proof cryoablation apparatus for treating different anatomical curvatures extends cryotherapy from a rigid needle-like application to a wide range of diagnostic and therapeutic procedures. An exemplary application is endovascular based cardiac ablation to create elongate continuous lesions. As described herein, creating elongate continuous lesions in certain locations of the heart can serve to treat various conditions such as, for example, atrial fibrillation or atrial flutter.

The Cox maze procedure to treat atrial fibrillation has been performed using radio frequency ablation catheters in both transthoracic epicardial approaches and transvascular endocardial approaches.

In transthoracic epicardial approaches, catheters or small probes are used to create linear lesions in the heart wall along lines corresponding to the maze of the Cox maze procedure. In the transvascular endocardial approaches, a catheter is navigated through the vasculature of the patient to the atrium, pressed against the inner wall of the atrium, and energized to create lesions corresponding to the maze of the Cox maze procedure.

Figure 31:
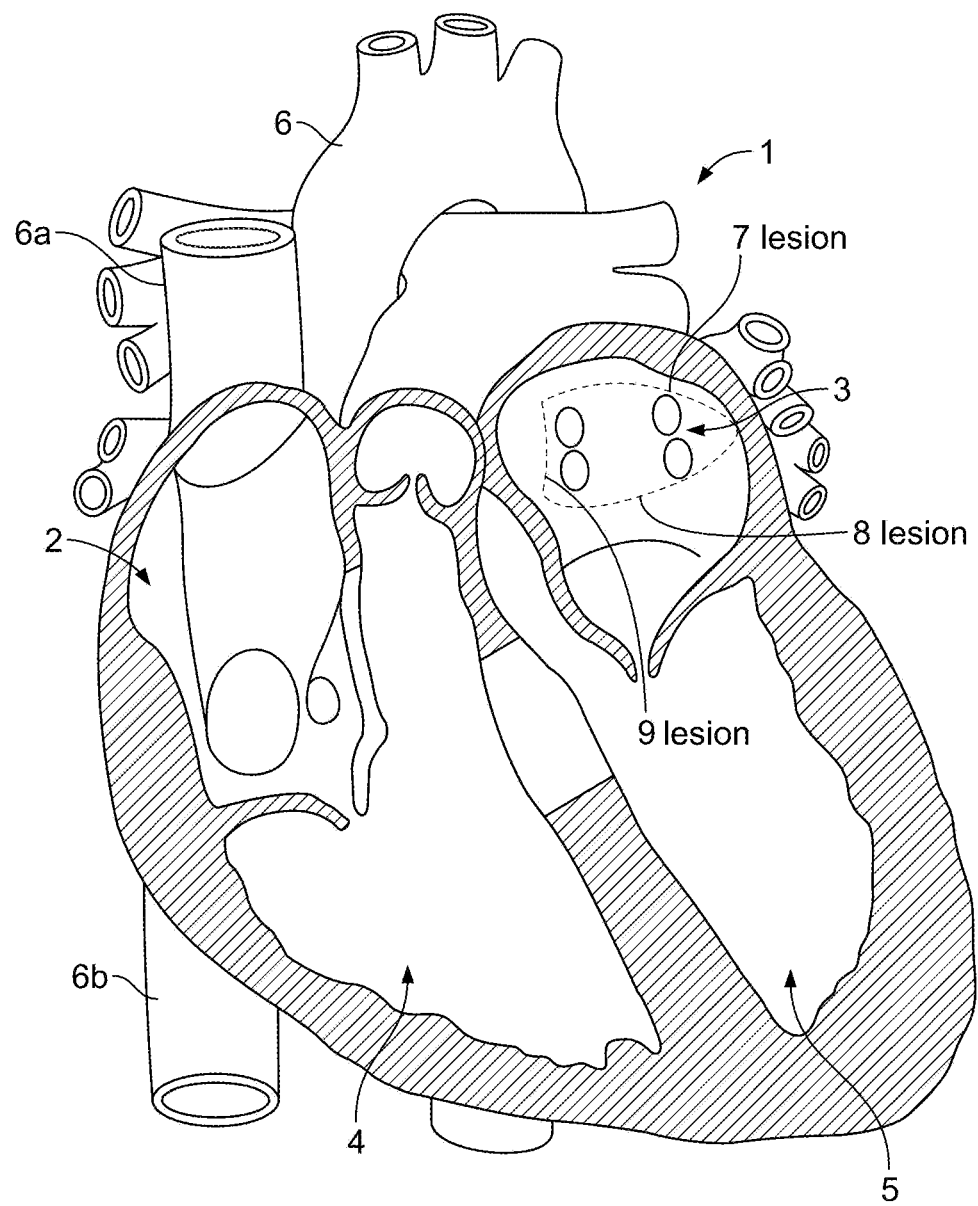
FIG. 31 is an illustration of a heart, and locations of various target lesions.

FIG. 31 shows examples of target sections of tissue and lesions in a Cox Maze procedure. Basic structures of the heart include the right atrium 2, the left atrium 3, the right ventricle 4 and the left ventricle 5. Catheters may be inserted into these chambers of the heart through various vessels, including the aorta 6 (accessed through the femoral artery), the superior vena cava 6a (accessed through the subclavian veins) and the inferior vena cava 6b (accessed through the femoral vein), and inferior vena cava entry 6c.

The following discussion will focus on embodiments for performing the left atrium lesion of the Cox maze VII procedure, but the procedure for producing these lesions can be used to create other lesions in an around the heart and other organs. Additional lesions of the Cox maze VII procedure, as well as other variations of the Cox Maze treatments may be carried out using steps and devices described herein. Additional techniques and devices are described in international patent application nos. PCT/US2012/047484 to Cox et al. and PCT/US2012/047487 to Cox et al. corresponding to International Publication Nos. WO 2013/013098 and WO 2013/013099 respectively.

In FIG. 31, a few of the left atrium lesions of the Cox maze VII lesion are illustrated. Cox maze lesions 7, 8 and 9 are shown on the inner wall of the left atrium of a heart 1. These correspond to the superior left atrial lesion (item 7) spanning the atrium over the left and right superior pulmonary vein entries into the atrium, the inferior left atrial lesion (item 8) spanning the atrium under the left and right inferior pulmonary vein entries into the atrium, and the vertical lesion (item 9) connecting the superior left atrial lesion and inferior left atrial lesion so that the right pulmonary veins are within the area defined by the lesions.

Figure 32:
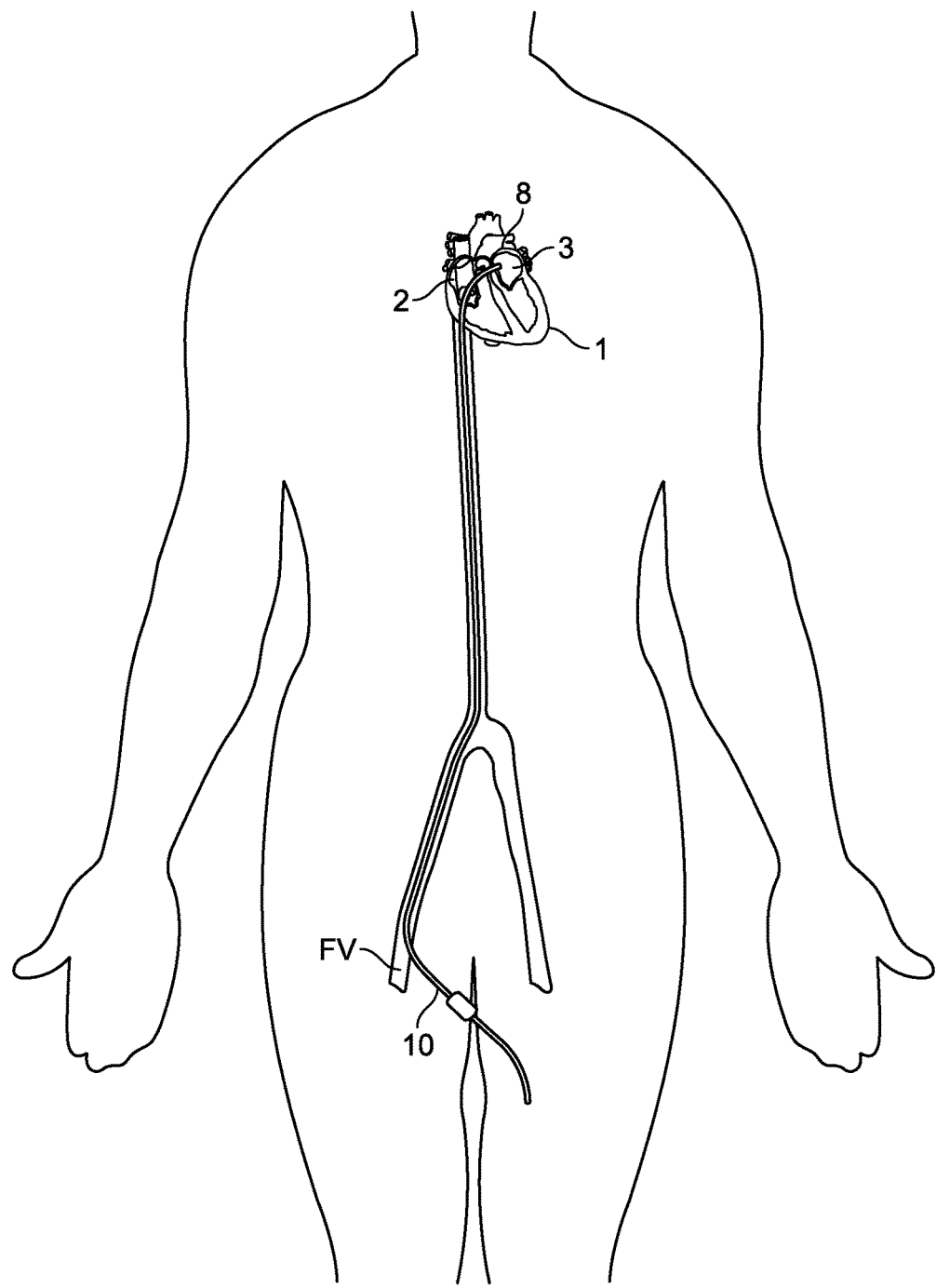
FIG. 32 is an illustration of a endovascular catheterization to access the heart.

FIG. 32 illustrates one technique to reach the left atrium with the distal treatment section of a catheter. A peripheral vein (such as the femoral vein FV) is punctured with a needle. The puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter 10 or sheath is introduced through the hemostatic valve of the introducer sheath and is advanced along the peripheral vein, into the target heart region (e.g., the vena cavae, and into the right atrium 2). Fluoroscopic imaging can be used to guide the catheter to the selected site.

Once in the right atrium 2, the distal tip of the guiding catheter is positioned against the fossa ovalis in the intraatrial septal wall. A needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for devices and catheters through its own inner lumen and into the left atrium.

Other left atrial access methods may be suitable substitutes for using the ablation device assembly of the present invention. In one alternative, a "retrograde" approach may be used, wherein the guiding catheter is advanced into the left atrium from the arterial system. In this variation, the Seldinger technique may be employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Figure 33:
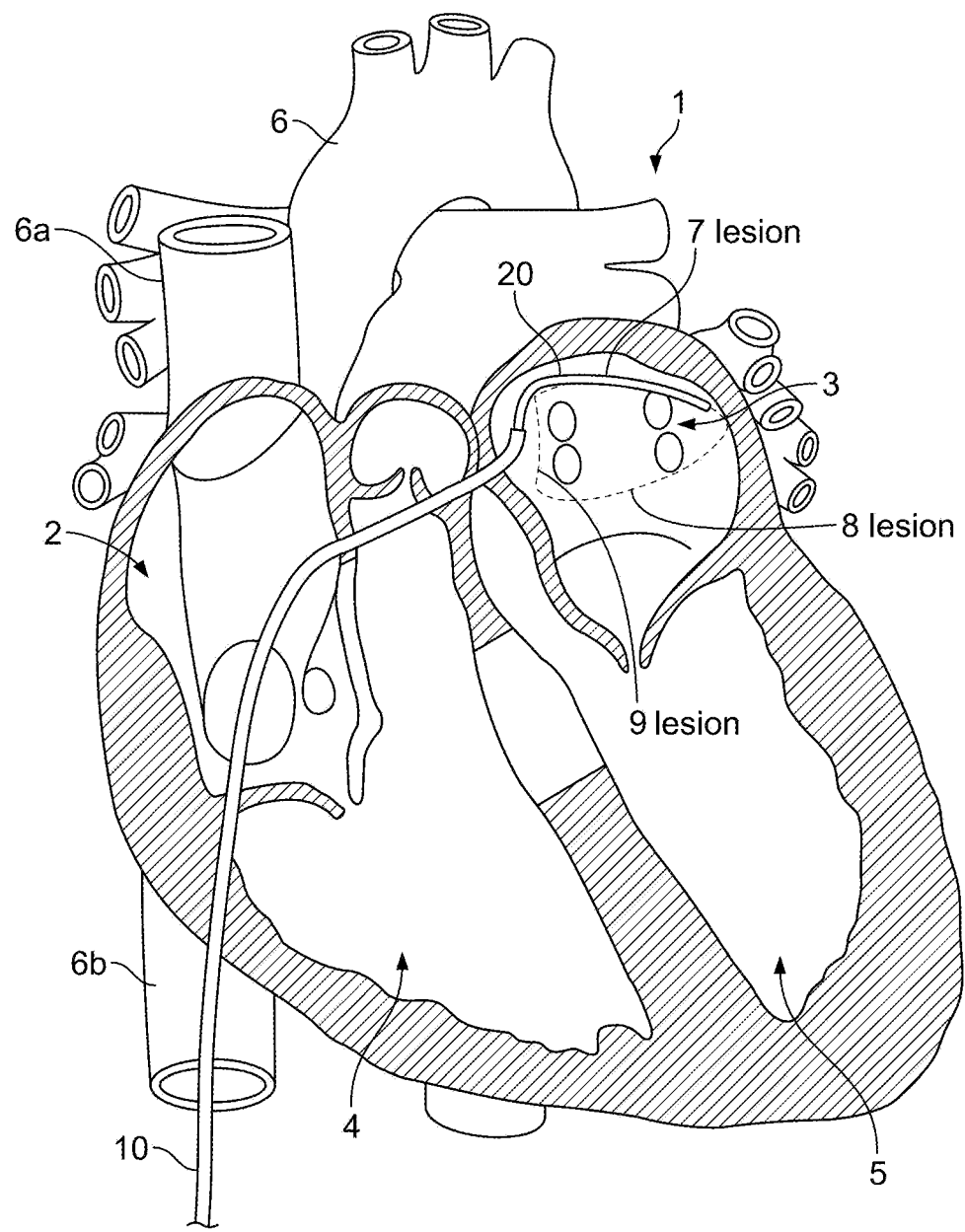
FIG. 33 is an illustration of a distal section of a cryoablation catheter placed in a chamber of the heart.

As shown in FIG. 33, an endocardial catheter 20 has been advanced through the guide catheter 10 and deployed as described herein to establish the desired line of a lesion of the left atrium. The distal segment of the endocardial catheter 20 is deflected within the endocardial space, preferably contacting the endocardial wall of the left atrium. This is illustrated in FIG. 33, where the distal treatment section has been configured and deflected to cover the superior left atrial lesion 7.

An exemplary lesion has a length ranging from 2-10 cm., and more preferably between 5-8 cm.

In embodiments, the device and method is adapted and intended to create a lesion 1) spanning the atrium over the left and right superior pulmonary vein entries into the atrium, 2) under the left and right inferior pulmonary vein entries into the atrium and/or 3) a vertical lesion on the right of the right superior and inferior vein entries into the atrium. The lesions are preferably continuous and linear, not a series of spots such as in some prior art point-ablation techniques. In accordance with the designs described above, the cryoenergy and heat transfer is focused on the endocardium, and intended to create the lesion completely through the endocardium.

Figure 34A:
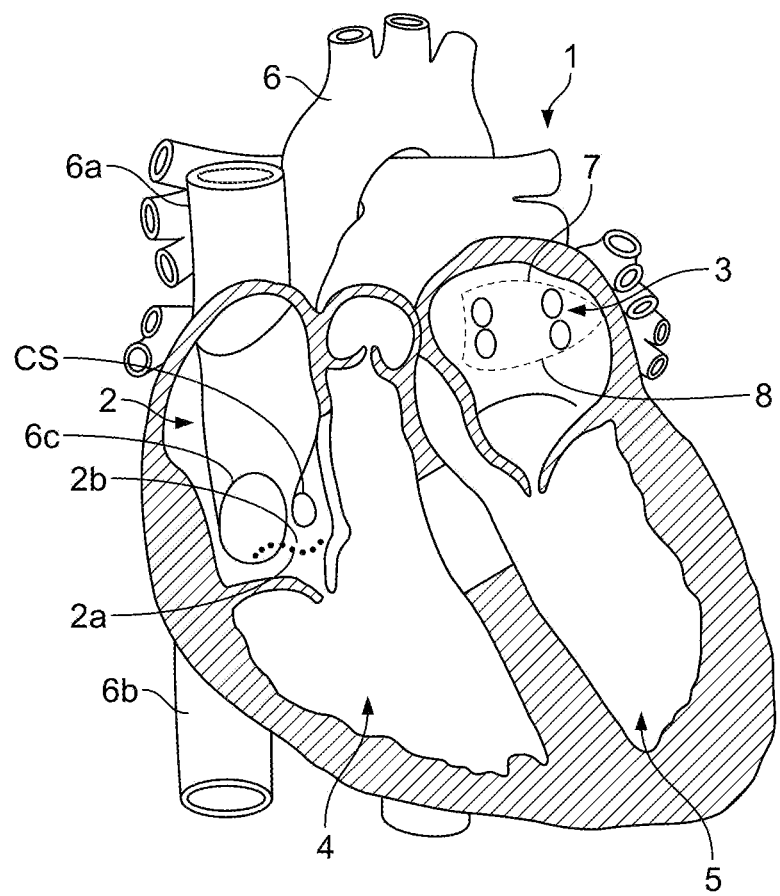
FIG. 34a is an illustration of a heart, and a location of a target lesion across the cavo-tricuspid isthmus of the right atrium.

FIG. 34a shows a target lesion 2a in the right atrium. In particular, lesion 2a is in the vicinity of the coronary sinus (CS) and the cavo tricuspid isthmus (CTI) 2b. Such a lesion has been found to affect the abnormal electrical activity in the heart associated with atrial flutter.

Figure 34B:
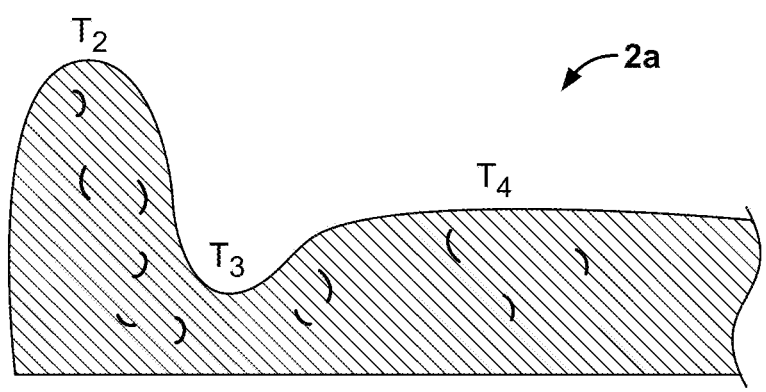
FIG. 34b is an illustration of a target tissue profile.

Placing a lesion across the CTI, however, is not straightforward. The difficulty arises because the CTI has an uneven profile. With reference to FIG. 34b, for example, an exemplary CTI profile is shown. Anticipated regions in the CTI include a peak T2, trough T3, and a flat T4. Additionally, the CTI profile of one individual may not match the CTI profile of another individual. Consequently, creating an elongate continuous lesion across this CTI surface is difficult.

The catheters and instruments described herein provide a solution to overcome the challenges described above in connection with treating an uneven anatomical surface such as the CTI region.

With reference to FIGS. 35a-35d, a cryoablation catheter 1200 includes an elongate shaft surrounded by an outer sleeve 1220. The inner elongate shaft includes a distal treatment section. The distal treatment section is shown being ejected from the outer sleeve 1220 in stages, or over a sequence of steps. In this embodiment the distal treatment section includes a plurality of fluid transport tubes to transport a cryogen to and from the treatment section. Preferably the transport tubes are shape set or preformed to assume the various predetermined shapes. And, each of the predetermined shapes is assumed based on the travel distance that the distal treatment section is ejected from the outer sleeve 1220, as described further below.

Figure 35C:
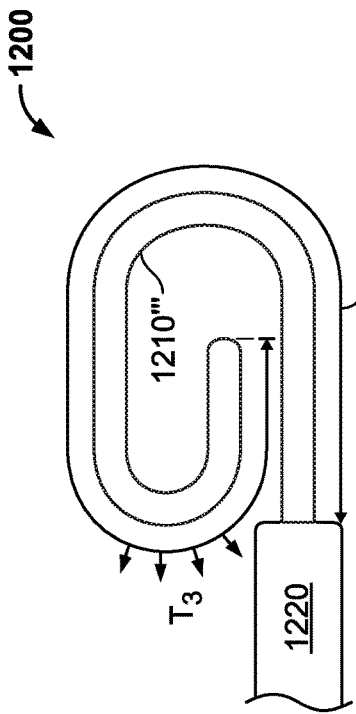
FIGS. 35a-35d illustrate a distal section of a catheter assuming a plurality of different shapes.
Figure 35D:
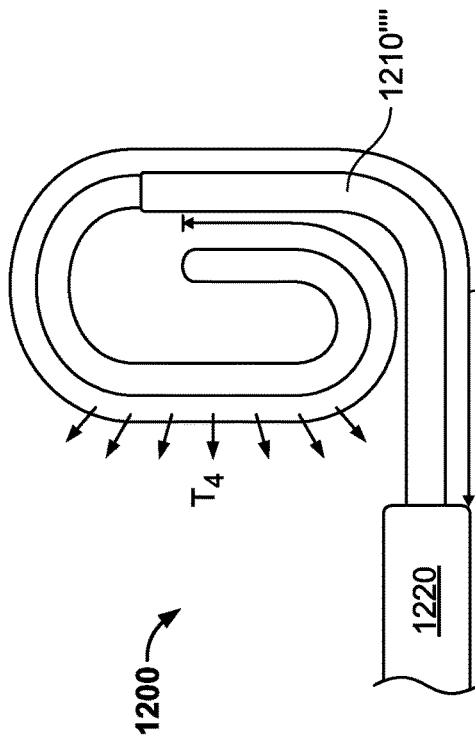
Figure 35A:
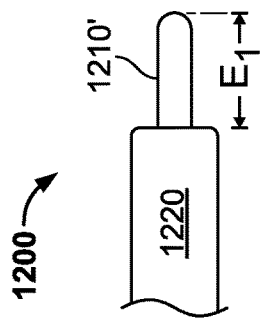

Initially, and with reference to FIG. 35a, treatment section 1210' is ejected a short travel distance E1 from the outer sleeve 1220. This is an intermediate position prior to forming the first treatment shape shown in FIG. 35b.

Figure 35B:
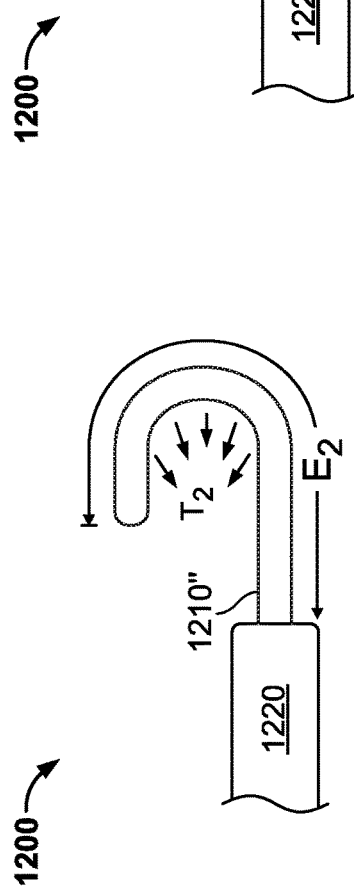

FIG. 35b shows treatment section 1210" ejected a travel distance E2 from the outer sleeve 1220. Travel distance E2 is the path length of ejection or distance traveled. As the distal treatment section reaches travel distance E2, it assumes the first treatment shape shown in FIG. 35b. This is a first treatment shape 1210" and includes a concave treatment portion T2 for treating the corresponding peak portion of the CTI anatomy shown in FIG. 34b. The distal section may be positioned on top of the peak of the CTI. Cooling energy is delivered to the catheter to ablate the target area. And, because blood is flowing through the heart, and the flowing blood acts as a heat sink, only the portion of the distal treatment section of the catheter in contact with the tissue reaches the cryo therapeutic temperature. The portions not in contact with the tissue are exposed to the relatively warm moving blood, and do not reach the cryo therapeutic temperature. Thus, there is little or no collateral damage.

FIG. 35c shows treatment section 1210'" further advanced from the outer sleeve 1220. Treatment section is shown ejected a travel distance E3 from the outer sleeve 1220. The treatment section assumes a loop-like shape as it winds up to its preset shape. This second treatment shape includes a convex treatment area T3 for treating the corresponding trough or valley portion of the CTI anatomy shown in FIG. 34b. The catheter is manipulated in situ to place section T3 of the catheter into the trough of the CTI shown in FIG. 34b. Energy is applied to cool the target section T3.

FIG. 35d shows treatment section 1210"" further ejected a travel distance E4 from the outer sleeve 1220. This is a third treatment shape and includes a flat treatment area T4 for treating the corresponding flat of the CTI anatomy shown in FIG. 34b. Energy is applied to cool the flat section T4.

Following the three or more applications of cooling energy to the CTI, the physician may observe whether a complete transmural lesion has been formed by observing the tissue as described above. Iceball formation may be observed using various imaging modalities. In embodiments, one or more freezes are performed and each freeze having a duration of up to two minutes.

Desirable lengths for the treatment regions T2, T3, and T4 range from 2-10 cm. or preferably 3.5 to 5 cm.

In order to achieve such treatment shapes and sizes, the length or travel distance of the treatment section of the shaft may range from 2-20 cm. and preferably 3-15 cm.

Preferably, in embodiments, the catheters achieve cooling power without vapor lock by transporting the cooling fluid near its critical point in the phase diagram. The distal treatment section designs described herein are intended for creating elongate continuous lesions spanning the full thickness of the heart wall, and in a safe manner to mitigate collateral damage in the event of a cryogen leak. The heat sink associated with the warm blood flow through the chambers of the heart is mitigated or avoided altogether because the ablation catheter is positioned within the heart chamber and directs the treating energy from the endocardium to the pericardium, or from the inside out.

Multiple endovascular products are described herein having a number of advantages including, for example: a) maintaining pressures of near-critical nitrogen below the maximum tolerance of ~600 psi for endovascular catheter material, b) containing leaks to eliminate the dangers arising there from, and c) controllably deploying distal treatment sections to treat a plurality of tissue areas having different curvatures. A cardiac ablation catheter in accordance with the principals of the present invention can be placed in direct contact along the internal lining of the left or right atrium, thereby avoiding most of the massive heat-sink of flowing blood inside the heart as the ablation proceeds outward.

Additionally, catheter configurations include substantial bends, or loops which provide both the circumferential, as well as linear, ablations to mimic the surgical Maze procedure noted above. The catheters described herein may be manipulated to form ring shaped lesions near or around the pulmonary vessel entries, for example.

The devices described herein may have a wide variety of applications including, for example, endoscopic cryotherapy. Candidate tumors to be ablated with cryoenergy include target tissues and tumors in the bronchial tree or lung as well as tissues in the upper and lower GI. The devices described herein may also be applied to destroy or limit target tissues in the head and neck.

Many modifications and variations of the present invention are possible in light of the above teachings. It is, therefore, to be understood that within the scope of the appended claims, the invention may be practiced otherwise than as specifically described.

We claim:

1. A cryoablation catheter for creating an elongated lesion along a cavo tricuspid isthmus, the cryoablation catheter comprising:

an outer sleeve having a sleeve proximal end, a sleeve distal end and an internal lumen; and an elongated shaft having a shaft proximal end, a shaft distal end and a distal treatment section adjacent the shaft distal end, the distal treatment section being axially slidable within the internal lumen of the outer sleeve and comprising:

a first predetermined shape that automatically forms when the distal treatment section is ejected from the internal lumen of the outer sleeve at a first distance;

a second predetermined shape that automatically forms subsequent to the first predetermined shape when the distal treatment section is ejected from the internal lumen of the outer sleeve at a second distance; and a third predetermined shape that automatically forms subsequent to the second predetermined shape when the distal treatment section is ejected from the internal lumen of the outer sleeve at a third distance,
wherein the first predetermined shape commences at the shaft distal end and terminates at a first bend and is configured to match a first region of the cavo tricuspid isthmus comprising a peak portion,
wherein the second predetermined shape is configured to match a second region of the cavo tricuspid isthmus different than the first region of the cavo tricuspid isthmus and comprising a trough portion, and
wherein the third predetermined shape comprises a flat section commencing at the first bend and terminating at a second bend and is configured to match a third region of the cavo tricuspid isthmus different than the first and second region of the cavo tricuspid isthmus, and
wherein the third predetermined shape has a loop-like structure formed as the shaft distal end and the first bend loop back towards a more proximal portion of the distal treatment section.

2. The cryoablation catheter of claim 1, wherein:
the first predetermined shape of the distal treatment section comprises a concave treatment surface,
the second predetermined shape of the distal treatment section comprises a convex treatment surface, and
the third predetermined shape of the distal treatment section comprises a substantially linear treatment surface.

3. The cryoablation catheter of claim 1, wherein lengths for each of the first predetermined shape, the second predetermined shape, and the third predetermined shape range from 3.5-5 cm.

4. The cryoablation catheter of claim 3, wherein the shaft distal end is ejected from 3 to 15 cm from the sleeve distal end.

5. The cryoablation catheter of claim 1, wherein the elongated shaft comprises a plurality of fluid transport tubes to transport a cryogen to and from the distal treatment section.

6. A method of creating a plurality of lesions in target tissue, the method comprising:
providing an ablation catheter comprising:
an outer sleeve having a sleeve proximal end, a sleeve distal end and an internal lumen; and
an elongated shaft having a shaft proximal end, a shaft distal end and a distal treatment section adjacent the shaft distal end, the distal treatment section being axially slidable within the internal lumen of the outer sleeve and comprising:
a first predetermined shape commencing at the shaft distal end and terminating at a first bend, and configured to match a peak portion in the target tissue and that automatically forms when the distal treatment section is ejected from the internal lumen of the outer sleeve a first distance;
a second predetermined shape configured to match a valley portion in the target tissue and that automatically forms when the distal treatment section is further ejected from the internal lumen of the outer sleeve a second distance; and
a third predetermined shape comprising a flat portion commencing at the first bend and terminating at a second bend, and configured to match a flat portion in the target tissue and that automatically forms when the distal treatment section is further ejected from the internal lumen of the outer sleeve a third distance and wherein the third predetermined shape has a loop-like structure and wherein the shaft distal end and the first bend loop back towards a more proximal portion of the distal treatment section,
percutaneously inserting the ablation catheter into a patient's vasculature;
advancing a distal section of the ablation catheter to the target tissue;
ejecting the distal treatment section of the elongated shaft from the outer sleeve a first distance causing the distal treatment section ejected from the outer sleeve to form the first predetermined shape,
contacting a first region of the target tissue with the first predetermined shape;
activating the ablation catheter to create a first lesion in the first region of the target tissue;
ejecting the distal treatment section of the elongated shaft from the outer sleeve the second distance causing the distal treatment section ejected from the outer sleeve to form the second predetermined shape;
contacting a second region of the target tissue with the second predetermined shape; and
activating the ablation catheter to create a second lesion in the second region of the target tissue.

7. The method of claim 6, wherein the target tissue is cardiac tissue.

8. The method of claim 6, wherein the plurality of lesions form a continuous, elongated lesion.

9. The method of claim 6, wherein the steps of ejecting are performed by retracting the outer sleeve over the elongate shaft to expose lengths of the distal treatment section.

10. The method of claim 6, wherein the elongated shaft comprises a plurality of fluid transport tubes to transport a cryogen to and from the distal treatment section.

11. The method of claim 6, further comprising the steps of:
ejecting the distal treatment section of the elongated shaft from the outer sleeve at a third distance causing the distal treatment section ejected from the outer sleeve to form said third predetermined shape;
contacting a third region of the target tissue with the flat portion of the third predetermined treatment shape; and
activating the ablation catheter to create a third lesion in the third region of the target tissue.

12. The method of claim 11, wherein:
the target tissue is a cavo tricuspid isthmus;
the first predetermined treatment shape comprises a concave portion that follows the first region of the cavo tricuspid isthmus;
the second predetermined treatment shape comprises a convex portion that follows the second region of the cavo tricuspid isthmus; and
the third predetermined treatment shape comprises a linear portion that follows the third region of the cavo tricuspid isthmus.

13. The method of claim 12, wherein lengths for each of the first predetermined shape, the second predetermined shape, and the third predetermined shape range from 3.5-5 cm.

14. The method of claim 13, wherein the shaft distal end is ejected from 3 to 15 cm from the sleeve distal end.

* * * * *